United States Patent
Horie et al.

(10) Patent No.: US 7,582,732 B2
(45) Date of Patent: Sep. 1, 2009

(54) LY6H POLYPEPTIDE

(75) Inventors: Masato Horie, Naruto (JP); Keiichi Okutomi, Tokushima (JP); Yoshihiro Taniguchi, Tokushima (JP); Mikio Suzuki, Tokushima (JP); Yutaka Ohbuchi, Tokushima (JP)

(73) Assignee: Osaka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/167,288

(22) Filed: Jul. 3, 2008

(65) Prior Publication Data

US 2008/0275218 A1 Nov. 6, 2008

Related U.S. Application Data

(60) Division of application No. 10/743,018, filed on Dec. 23, 2003, now Pat. No. 7,432,363, which is a continuation of application No. 09/787,360, filed on Mar. 16, 2001, now abandoned.

(51) Int. Cl.
C07K 14/00 (2006.01)
C12P 21/06 (2006.01)
C12N 15/00 (2006.01)

(52) U.S. Cl. .................... 530/350; 435/69.1; 435/320.1

(58) Field of Classification Search ........................ None
See application file for complete search history.

(56) References Cited

U.S. PATENT DOCUMENTS 5,011,912 A 4/1991 Hopp et al.

2002/0091244 A1 7/2002 Lal et al.

FOREIGN PATENT DOCUMENTS

JP 3-48696 A 3/1991
WO 97/18224 A1 5/1997

OTHER PUBLICATIONS

Horie et al, Genomics, 53:365-368 (1998).
Fleming et al, J. of Immunology, 150(12):5379-5390 (1993).
Friedman et al, Immunogenetics, 31:104-111 (1990).
Graubert et al, Blood, 90:145B (1997).
Gumley et al, Immunology and Cell Biology, 73(4):277-296 (1995).
Nosten-Bertrand et al, Nature, 379:826-829 (1996).
Armstrong et al, J. Comparative Neurology, 216:53-68 (1983).
Brakenhoff et al, J. of Cell Biol., 129(6):1677-1689 (1995).
Mao et al, Proc. Natl. Acad. Sci. USA, 93:5910-5914 (1996).
Cray et al, Molecular Brain Res., 8:9-15 (1990).
Skolnick et al., TIBTECH, 18:34-39 (2000).
Bork et al., Current Opinion in Structural Biology, 8:331-332 (1998).
Fujiwara et al, "Human fetal brain cDNA 5'-end Gen-425G08", GenBank Database Accession No. D61641, Aug. 31, 1995.

*Primary Examiner*—Olga N Chernyshev
(74) *Attorney, Agent, or Firm*—Sughrue Mion, PLLC

(57) ABSTRACT

The invention provides a brain-specific gene useful in treating Alzheimer's disease, for instance, which comprises a nucleotide sequence cording for the amino acid sequence shown in SEQ ID NO:1 and fragments thereof; an expression vector comprising the gene; a host cell comprising the expression vector; an expression product of the gene; an antibody against the product; a therapeutic and prophylactic composition for neurodegenerative disease; and the like.

2 Claims, 1 Drawing Sheet

```
                          SEQUENCE LISTING

<160> NUMBER OF SEQ ID NOS: 3

<210> SEQ ID NO 1
<211> LENGTH: 140
<212> TYPE: PRT
<213> ORGANISM: Homo sapines
<220> FEATURE:
<221> NAME/KEY: misc_feature
<223> OTHER INFORMATION: human embryonic brain

<400> SEQUENCE: 1

Met Leu Pro Ala Ala Met Lys Gly Leu Gly Leu Ala Leu Leu Ala Val
1               5                   10                  15

Leu Leu Cys Ser Ala Pro Ala His Gly Leu Trp Cys Gln Asp Cys Thr
            20                  25                  30

Leu Thr Thr Asn Ser Ser His Cys Thr Pro Lys Gln Cys Gln Pro Ser
        35                  40                  45

Asp Thr Val Cys Ala Ser Val Arg Ile Thr Asp Pro Ser Ser Ser Arg
    50                  55                  60

Lys Asp His Ser Val Asn Lys Met Cys Ala Ser Ser Cys Asp Phe Val
65                  70                  75                  80

Lys Arg His Phe Phe Ser Asp Tyr Leu Met Gly Phe Ile Asn Ser Gly
                85                  90                  95

Ile Leu Lys Val Asp Val Asp Cys Cys Glu Lys Asp Leu Cys Asn Gly
            100                 105                 110

Ala Ala Gly Ala Gly His Ser Pro Trp Ala Leu Ala Gly Gly Leu Leu
        115                 120                 125

Leu Ser Leu Gly Pro Ala Leu Leu Trp Ala Gly Pro
    130                 135                 140

<210> SEQ ID NO 2
<211> LENGTH: 420
<212> TYPE: DNA
<213> ORGANISM: Homo sapiens
<220> FEATURE:
<221> NAME/KEY: misc_feature
<223> OTHER INFORMATION: human embryonic brain

<400> SEQUENCE: 2
atgctgcctg cagccatgaa gggcctcggc ctggcgctgc tggccgtcct gctgtgctcg      60
gcgcccgctc atggcctgtg gtgccaggac tgcaccctga ccaccaactc cagccattgc     120
accccaaagc agtgccagcc gtccgacacg gtgtgtgcca gtgtccgaat caccgatccc     180
agcagcagca ggaaggatca ctcggtgaac aagatgtgtg cctcctcctg tgacttcgtt     240
aagcgacact ttttctcaga ctatctgatg gggtttatta actctgggat cttaaaggtc     300
gacgtggact gctgcgagaa ggatttgtgc aatgggcgg caggggcagg gcacagcccc      360
tgggccctgg ccggggggct cctgctcagc ctggggcctg ccctcctctg ggctgggccc     420

<210> SEQ ID NO 3
<211> LENGTH: 854
<212> TYPE: DNA
<213> ORGANISM: Homo sapiens
```

```
<220> FEATURE:
<221> NAME/KEY: misc_feature
<223> OTHER INFORMATION: human embryonic brain
<220> FEATURE:
<221> NAME/KEY: exon
<222> LOCATION: (99)..(518)

<400> SEQUENCE: 3
acgccgcccg agcccggagt gcggacaccc ccgggatgct tgcgcccag aggacccgcg        60 ccccaagccc ccgcgccgcc cccaggccca cccggagc atg ctg cct gca gcc atg      116
                                          Met Leu Pro Ala Ala Met
                                          1               5 aag ggc ctc ggc ctg gcg ctg ctg gcc gtc ctg ctg tcg gcg ccc            164
Lys Gly Leu Gly Leu Ala Leu Leu Ala Val Leu Leu Cys Ser Ala Pro
            10                  15                  20 gct cat ggc ctg tgg tgc cag gac tgc acc ctg acc acc aac tcc agc        212
Ala His Gly Leu Trp Cys Gln Asp Cys Thr Leu Thr Thr Asn Ser Ser
        25                  30                  35 cat tgc acc cca aag cag tgc cag ccg tcc gac acg gtg tgt gcc agt        260
His Cys Thr Pro Lys Gln Cys Gln Pro Ser Asp Thr Val Cys Ala Ser
    40                  45                  50 gtc cga atc acc gat ccc agc agc agc agg aag gat cac tcg gtg aac        308
Val Arg Ile Thr Asp Pro Ser Ser Ser Arg Lys Asp His Ser Val Asn
55                  60                  65                  70 aag atg tgt gcc tcc tcc tgt gac ttc gtt aag cga cac ttt ttc tca        356
Lys Met Cys Ala Ser Ser Cys Asp Phe Val Lys Arg His Phe Phe Ser
                75                  80                  85 gac tat ctg atg ggg ttt att aac tct ggg atc tta aag gtc gac gtg        404
Asp Tyr Leu Met Gly Phe Ile Asn Ser Gly Ile Leu Lys Val Asp Val
            90                  95                  100 gac tgc tgc gag aag gat ttg tgc aat ggg gcg gca ggg gca ggg cac        452
Asp Cys Cys Glu Lys Asp Leu Cys Asn Gly Ala Ala Gly Ala Gly His
        105                 110                 115 agc ccc tgg gcc ctg gcc ggg ggg ctc ctg ctc agc ctg ggg cct gcc        500
Ser Pro Trp Ala Leu Ala Gly Gly Leu Leu Leu Ser Leu Gly Pro Ala
    120                 125                 130 ctc ctc tgg gct ggg ccc tgatgtctcc tccttcccac ggggcttctg               548
Leu Leu Trp Ala Gly Pro
135                 140 agcttgctcc cctgagcctg tggctgccct ctccccagcc tggcgtggct ggggctgggg      608
gcagccttgg cccagctccg tggctgtggc ctgtggctct cactcctccc ccgacgtgaa      668
gcctccctgt ctctccgcca gctctgagtc ccaggcagct ggacatctcc aggaaaccag      728
gccatctggg caggaggcct ggggatgagg gtgggggggg accccaggt cccggagggg       788 aagtgaagca acagcccagc tggaagggcg tcttctgcgg agaaataaag tcacttttga      848
gtcctg                                                                 854
```

LY6H POLYPEPTIDE

This Application is a Divisional of U.S. application Ser. No. 10/743,018, filed Dec. 23, 2003 (now allowed), which in turn is a Continuation of U.S. application Ser. No. 09/787,360, filed Mar. 16, 2001 (now abandoned), which in turn is a 371 of PCT/JP99/05039, filed Sep. 16, 1999; the disclosure of each of which is incorporated herein by reference.

TECHNICAL FIELD

The invention relates to a gene expressed with high specificity at a high level in the brain, more particularly a gene coding for a novel protein belonging to the Ly6 Family (cf. the literature cited below) which has been utilized in the purification of blood stem cells, studies on the differentiation of blood cells, activation of immune cells, inhibition of production of active immune cells, treatment of tumors and the like. The invention further relates to a novel protein encoded by said gene and to its specific antibody. In addition, the invention relates to a therapeutic and prophylactic composition for neurodegenerative disease such as Alzheimer's disease.

BACKGROUND ART

Proteins of the Ly6 family have a low-molecular weight GPI-anchored structure and have been identified as a class of cell surface glycoproteins forming a gene cluster on mouse chromosome 15 [Proc. Natl. Acad. Sci., USA., 84, 1638-1643 (1987)].

The Ly6 family is specifically expressed at high levels in bone marrow cells and lymphoid cells and, therefore, has been utilized as a marker for T-cell differentiation and hematopoietic stem cells [Immunol. Cell Biol., 73, 277-296 (1995)]. While much remains to be known about its functions in vivo, the finding that its expression is highly modulated in the lymphocytic system suggests that these proteins are playing important roles in the immune system, particularly in the differentiation and function of T cells. It is reported that Ly6c, for instance, mediates the homing of $CD8^+$ T cells to the lymph node through integrin-dependent adhesion [Proc. Natl. Acad. Sci., USA., 94, 6898-6903 (1997)].

Furthermore, many GPI-anchored proteins are known to interact with protein kinases [Science, 254, 1016-1019 (1991)]. For example, the interaction of Ly6 with p56lck and p59fyn suggests the likelihood of its involvement in the signal transduction of T cells [Eur. J. Immunol., 23, 825-831 (1993)]. It is also reported that T cells derived from Ly6a-defective mice have been enhanced in the ability to proliferate in response to antigenic stimulation [J. Exp. Med., 186, 705-717 (1997)]. The possibility of its regulating not only the activation of T cells but also that of B cells has also been suggested [J. Immunol., 144, 2197-2204 (1990)].

Furthermore, several GPI-anchored proteins are known to have been expressed and be functioning in both the lymphocytic system and the nervous system [Nature, 379, 826-829 (1996); Curr. Biol., 7, 705-708 (1997)]. In the Ly6 family, Ly6a.2 and Ly6E are reportedly present and functioning in both systems [Proc. Natl. Acad. Sci., USA., 85, 2255-2259 (1996); J. Immunol, 157, 969-973 (1996)].

Elucidation of the physiological roles played by such proteins of the Ly6 family and the genes coding for the proteins and the resulting information are considered to be of use in the field of fundamental scientific research as well as in the pharmaceutical field in connection with the purification of blood stem cells, studies on the differentiation of blood cells, activation of immune cells, inhibition of activation of immune cells, therapy of tumors, and the like.

Recently, in patients with Alzheimer's disease, an excessive cerebral temporal lobe atrophy as compared with age-associated brain atrophy has been reported [Jobst, K. A., et al., Lancet, 343, 829-830 (1994)], suggesting that some gene or genes having a bearing on the cerebral temporal lobe are somehow associated with the onset and progression of Alzheimer's disease. It is logical to assume that should such a gene be identified or characterized, there might be provided information useful for the therapy and prophylaxis of Alzheimer's disease.

Therefore, an object of the present invention is to provide the above information needed by those concerned, particularly a novel human protein belonging to the Ly6 family and a gene coding for the protein.

A further object of the invention is to provide a pharmaceutical composition for the therapy and prophylaxis of various neurodegenerative diseases, represented by Alzheimer's disease.

The present inventor explored into the genes derived from various human tissues and succeeded in isolating and characterizing a novel brain-specific gene meeting the above objects. The inventor found that the level of expression of this newly isolated gene is markedly depressed in the temporal lobe, inclusive of the hippocampus and entorhinal cortex, of a patient with Alzheimer's disease, that this is a causative factor in the onset and progression of Alzheimer's disease and in dementia and other disturbances and that this gene and its expression product can be exploited with advantage in the therapy and prophylaxis of Alzheimer's disease. The present invention has been accomplished on the basis of the above findings.

DISCLOSURE OF INVENTION

The present invention provides a gene comprising a nucleotide sequence coding for the following protein (a) or (b).

(a) a protein having the amino acid sequence shown in SEQ ID NO:1

(b) a protein having an amino acid sequence derived from the amino acid sequence shown in SEQ ID NO:1 by deletion, substitution or addition of one or a plurality of amino acids and having at least one physiological activity selected from the group consisting of neuronal survival-supporting activity, nerve elongating activity, nerve regenerating activity, neuroglia-activating activity, and mnemonic (brain memory-forming) activity.

The invention also provides the above gene wherein the nucleotide sequence is shown in SEQ ID NO:2, in particular, which is a human gene.

Furthermore, the invention provides a gene comprising the following polynucleotides (a) or (b), particularly the corresponding human gene.

(a) a polynucleotide containing the nucleotide sequence shown in SEQ ID NO:3

(b) a polynucleotide which hybridizes under stringent condition with a DNA having the nucleotide sequence shown in SEQ ID NO:3.

The invention further provides a gene expression vector harboring said gene; a host cell harboring said gene expression vector; an expression product which is expressed by said host cell; a protein encoded by the gene of the invention; and an antibody which binds said expression product or said protein.

The invention further provides a therapeutic and prophylactic composition for neurodegenerative disease, which comprises said protein or an equivalent thereof or said expression product as an active ingredient in combination with a pharmaceutical carrier. More particularly, the invention provides the therapeutic and prophylactic composition for neurodegenerative disease, wherein said active ingredient is a protein having the amino acid sequence shown in SEQ ID NO:1 or an equivalent thereof or a gene product obtainable by expression of the whole or part of a gene comprising a nucleotide sequence shown in SEQ ID NO:2 and having at least one physiological action selected from the group consisting of neuronal survival-supporting action, nerve elongating action, nerve-regenerating action, neuroglia-activating action, and brain memory-forming (mnemonic, encoding) action.

Especially, the invention provides the therapeutic and prophylactic composition for Alzheimer's disease, Alzheimer type dementia, brain ischemia and Parkinson's disease.

In addition, the invention provides a sense strand oligonucleotide comprising at least 20 consecutive constituent nucleotides of the nucleotide sequence shown in SEQ ID NO:2; a gene therapy composition comprising said sense strand oligonucleotide as an active ingredient in combination with a pharmaceutical carrier; and a gene-specific probe comprising an oligonucleotide sequence of at least 10 consecutive constituent nucleotides of the nucleotide sequence shown in SEQ ID NO:2.

Furthermore, the invention provides a method of screening for candidate compounds either capable of binding to said protein, equivalent thereof or expression product or influencing its activity which comprises using said protein, equivalent or expression product; a kit for said screening; and said compounds so screened.

Representation of amino acids, peptides, nucleotide sequences, nucleotides, etc. by abbreviations in the specification is in conformity with the rules recommended by IUPAC-IUB [IUPAC-IUB Communication on Biological Nomenclature, Eur. J. Biochem., 138, 9 (1984)], "Guideline for drafting patent specifications relative to nucleotide sequences and/or amino acid sequences" (edited by the Patent Office of Japan) and the conventions relating to the use of codes or symbols in the art.

A specific example of the gene of the invention is the gene deduced from the DNA sequence of the PCR product designated "LY6H" as described in the example which appears later herein. Its nucleotide sequence is as shown in SEQ ID NO:3.

The LY6H gene is a cDNA containing a 420-codon open reading frame (ORF) coding for a novel brain-specific protein (LY6H protein) having a 140-residue amino acid sequence as shown in SEQ ID NO:1, and having a full-length sequence of 854 nucleotides.

The LY6H protein which is the expression product of the gene of the invention was found to have high homology to mouse Ly6 family proteins [Immunol. Cell Biol., 73, 277-296 (1995)] by a GenBank/EMBL database search using FASTA Program (Person, W. R. et al., Proc. Natl. Acad. Sci., USA., 85, 2444-2448 (1988)). Furthermore, high gene-to-gene homology was recognized. Therefore, the gene of the invention is considered to be a novel human Ly6 gene.

The LY6 gene of the invention was identified to be a gene which is specifically expressed in the brain by the sequencing of more than 28000 cDNA clones selected at random from a fetal human brain cDNA library. By RH chromosome mapping [Hum. Mol. Genet., 5, 339-346 (1996)], the locus of the gene on the chromosome was found to be 8q24. 3.

Thus, the gene and expression product of the invention, thus provided, contribute to detection of the expression of the gene in various tissues, production of human LY6H protein by genetic engineering techniques, and construction of an antibody thereto, hence enabling the purification of hematopoietic stem cells, study of blood cell differentiation, activation or suppression of immune cells, therapy of tumors, and the like.

In addition, the expression product (polypeptide) of the invention, thus provided, enables provision of a drug for prophylaxis and therapy of neurodegenerative diseases such as Alzheimer's disease, Alzheimer type dementia, Parkinson's disease and ischemic brain. Furthermore, the sense strand of the gene according to the invention can be utilized as a pharmaceutical composition for gene therapy, with which the onset and progression of the above-mentioned neurodegenerative diseases can be inhibited or arrested.

The invention further provides a method of screening for compounds either binding or influencing the activity of the expression product (polypeptide) of the invention and a relevant kit for screening, hence compounds so screened as well. For identification of such compounds screened, an antibody binding to the expression product of the gene of the invention can be utilized.

In the specification, the term "gene" is used to mean a double-stranded DNA and its constituent single-stranded DNA, whether sense or antisense, without regard to its length. Therefore, unless otherwise indicated, the gene (DNA) of the invention includes a double-stranded DNA containing a human genomic DNA, a single-stranded DNA (sense strand) inclusive of the cDNA, a single-stranded DNA (antisense strand) having a sequence complementary to said sense strand, and fragments of said DNAs.

The gene (DNA) of the invention may contain a leader sequence, a coding region, exons and introns. The polynucleotide includes both RNA and DNA. The DNA includes cDNA, genomic DNA and synthetic DNA. The polypeptide includes its fragments, homologs, derivatives and mutants. The mutants include alleles which occur naturally, mutants not existing naturally, mutants having amino acid sequences mutated by deletion, substitution, addition and/or insertion, and mutants having functionally equivalent modified amino acid sequences.

Such modifications (e.g. mutations) of amino acid sequences may for example occur from spontaneous mutation or posttranslational modification but may be artificially induced by utilizing a native gene (for example, specific genes of the invention).

The homology of such mutants to the unmutated polypeptide may be at least 70%, preferably 80%, more preferably 95%, still more preferably 97%. The above polypeptide and its mutants and homologs have a structural feature conserved in common and may have the biological activities of the expression product of the gene of the invention, such as neuronal survival-supporting action, neuronal growth-stimulating action, nerve generating action, and neuroglia-stimulating action. The homology of polypeptides can be analyzed by searching through a database such as SWISSPLOTS Database using a sequence analysis software such as FASTA [Clustal, V., Methods Mol. Biol., 25, 307-318 (1994)].

The gene coding for such a mutant is silent or conserved for amino acid substitution. Thus, the amino acid residues encoded by the nucleotide sequence are not altered.

The conservatively substitutable amino acid residues, i.e. the amino acid residues substitutable with other amino acid residues without losing the activities of the polypeptide having such original amino acid residues, and the corresponding original amino acid residues are as follows.

| Original amino acid residue | Conservatively substituting amino acid residue |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn or Gln |
| Ile | Leu or Val |
| Leu | Ile or Val |
| Lys | Arg, Aln or Glu |
| Met | Leu or Ile |
| Phe | Met, Leu or Tyr |
| Ser | Thr |
| Thr | Ser |
| Trp | Tyr |
| Tyr | Trp or Phe |
| Val | Ile or Leu |

In addition, Cys may be substituted for a different kind of amino acid residue, e.g. Ser, Ala or Val.

The gene and expression product according to the invention provide information and means of great use for the elucidation, expatiation, diagnosis, prophylaxis and therapy of neurodegenerative diseases such as Alzheimer's disease, brain ischemia and Parkinson's disease. The gene of the invention can also be used with advantage for the development of new drugs capable of inducing expression of the gene for use in the treatment of said neurodegenerative diseases. In addition, the detection of expression of the gene of the invention and of the resulting expression product in individuals or tissues, and the detection of mutation (deletion or point mutation) of the gene or abnormal expression thereof can be utilized with advantage for the elucidation and diagnosis of said neurodegenerative diseases.

The gene of the invention includes but is not limited to the gene having the nucleotide sequence shown in SEQ ID NO:2 which codes for a protein having the amino acid sequence shown in SEQ ID NO:1, for example a gene (LY6H gene) having the nucleotide sequence shown in SEQ ID NO:3. For example, the gene of the invention may be a gene coding for an amino acid sequence derived from the above-defined amino acid sequence by a given modification, a gene coding for an amino acid sequence having a given degree of homology to the above-defined amino acid sequence, or a gene having a nucleotide sequence having a given degree of homology to any of the above genes.

The above-mentioned given degree of homology to a defined amino acid sequence or nucleotide sequence means a homology of at least not less than 70%, preferably not less than 90%, more preferably not less than 95%, still more preferably not less than 97%. The present invention encompasses homologs (gene homologs and protein homologs) having such homology.

The gene of the invention includes "a gene coding for a polypeptide having an amino acid sequence (modified amino acid sequence) derived from the amino acid sequence shown in SEQ ID NO:1 by deletion, substitution or addition of one or a plurality of amino acids". The extent and position or positions of "deletion, substitution or addition" are not particularly restricted insofar as the resulting polypeptide having a modified amino acid sequence is equivalent, in biological function, to the polypeptide (LY6H protein) having the amino acid sequence shown in SEQ ID NO:1. The biological "function" mentioned above includes physiological functions such as neuronal survival-supporting action, nerve elongating action, nerve regenerating action, neuroglia-activating action, and mnemonic action, and the "equivalent" is a polypeptide having such functions. Therefore, the protein having such a modified amino acid sequence includes a protein (equivalent) having a fragment (a consecutive-residue fraction) of the amino acid sequence shown in SEQ ID NO:1 and having physiological activities similar to those mentioned above for the full-length of said amino acid sequence. Furthermore, the gene coding for a polypeptide having the above-modified amino acid sequence may be a gene with which the gene of the invention encoding a polypeptide having the pre-modification amino acid sequence can be detected. The term plurality as used in connection with said modification usually means not less than 2 but up to several, although the range is not restrictive.

The homolog of LY6H gene (and the homolog of the expression product of the gene) according to the invention means any of a series of related genes (and their expression products) which are homologous in sequence and recognized as one gene family from their structural characteristics, common gene expression pattern, and similarities in said biological function. This, of course, includes alleles of the genes of the invention.

The modification (mutation) of an amino acid sequence may occur naturally, for example by spontaneous mutation and posttranslational modification but may be induced artificially on the basis of the native gene (for example the specific gene of the invention). The invention covers any and all modified genes having the above characteristics without regard to the cause or means of modification or mutation.

The artificial means for said modification (mutation) of the amino acid sequence includes genetic engineering techniques such as site-specific mutagenesis [Methods in Enzymology, 154, 350, 367-382 (1987); ibid., 100, 468 (1983); Nucleic Acids Res., 12, 9441 (1984); "Zoku Seikagaku Jikken Koza (Experiments in Biochemistry, Second Series) 1": Idenshi Kenkyuho (Methods in Gene Research) II, the Biochemical Society of Japan (ed.), p 105 (1986), etc.], methods of chemical synthesis such as the phosphotriester method and phosphoamidite method [J. Am. Chem. Soc., 89, 4801 (1967); ibid., 91, 3350 (1969); Science, 150, 178 (1968); Tetrahedron Lett., 22, 1859 (1981); ibid., 24, 245 (1983)], and combinations of such methods.

More particularly, the DNA can be synthesized by a chemical method such as the phosphoamidite method or the phosphotriester method, and this synthesis can be effected on a commercially available automated oligo-nucleotide synthesizer. The double-stranded fragment can be obtained from the chemically synthesized single-strand fragment by synthesizing a complementary strand and annealing them under suitable conditions or adding the complementary strand using a suitable primer sequence and a DNA polymerase.

A specific example of the gene according to the invention is the gene having the nucleotide sequence shown in SEQ ID NO:3. The coding region (the sequence shown in SEQ ID NO:2) of this nucleotide sequence is an example of combination of codons specifying the respective amino acid residues of the amino acid sequence shown under SEQ ID NO:1. The gene of the invention is not limited to the gene having said defined nucleotide sequence but includes any gene having a nucleotide sequence obtainable by selecting any arbitrary combination of codons for each amino acid residue. Selection of codons can be made in the routine manner, with reference to the codon usage in the host to be employed [Nucleic Acids Res., 9, 43 (1981)].

Furthermore, the gene of the invention includes one having a nucleotide sequence showing a certain level of homology to the nucleotide sequence shown in SEQ ID NO:3. Inferred by said level of homology are polynucleotides and complementary polynucleotides having at least 70% homology, preferably at least 90% homology, more preferably at least 95% homology, to the nucleotide sequence shown in SEQ ID NO:3. The gene having such a level of homology may for example be characterized as a polynucleotide which hybridizes with a DNA having the nucleotide sequence shown in SEQ ID NO:3 under stringent conditions. More particularly, the gene having a nucleotide sequence which hybridizes with the DNA having the nucleotide sequence shown in SEQ ID NO:3 under the condition of 6×SSC at 65° C. overnight or 50% formamide-4×SSC at 37° C. overnight is subsumed in the concept of the gene having said level of homology. Here, SSC stands for standard saline citrate (1×SSC=0.15 M NaCl, 0.015 M sodium citrate).

The gene of the invention can be easily produced and isolated by the general genetic engineering technology based on the sequence information on any specific example of the gene of the invention as disclosed in this specification [e.g. Molecular Cloning 2d Ed, Cold Spring Harbor Lab. Press (1989); Zoku Seikagaku Jikken Koza (Experiments in Biochemistry, Second Series): "Idenshi Kenkyuho (Methods in Gene Research) I, II, III, the Biochemical Society of Japan (ed.), (1986)].

More particularly, this can be done by preparing a cDNA library from a suitable source, in which the gene of the invention can be expressed, by a routine procedure and selecting a desired clone from this library using a suitable probe or antibody specific to the gene of the invention [Proc. Natl. Acad. Sci., USA., 78, 6613 (1981); Science, 222, 778 (1983)].

The source of cDNA, which can be used in the above procedure includes various cells and tissues expressing the gene of the invention, as well as cultured cells derived therefrom, particularly brain tissues. Isolation of the total RNA from such a source, isolation and purification of mRNA, and acquisition and cloning of cDNA can also be carried out in the conventional manner. Moreover, cDNA libraries are commercially available and the present invention can be carried into practice using such cDNA libraries, for example those cDNA libraries available from CLONTECH Lab. Inc.

The method of screening for the gene of the invention from a cDNA library is not particularly restricted but the conventional procedure can be employed. Examples of the screening methods include an immuno-screening method using a specific antibody to the protein produced by a cDNA to select the corresponding cDNA clone, a method using a probe selectively binding to the objective DNA sequence, such as a plaque hybridization method, and a colony hybridization method, and a combination of such methods.

As the probe for the above method, the DNA chemically synthesized according to the nucleotide sequence information on the gene of the invention can be generally employed. The gene of the invention which has already been obtained or a fragment thereof can also be used as the probe with advantage. The sense primer and antisense primer established according to the nucleotide sequence information on the gene of the invention can be used as screening probes.

The nucleotide sequence for use as the probe may be a partial nucleotide sequence corresponding to SEQ ID NO:2 and comprising at least 10 consecutive nucleotides, preferably 20 consecutive nucleotides, more preferably 30 consecutive nucleotides, most preferably 50 consecutive nucleotides. Moreover, the positive clone having the oligonucleotide sequence shown in SEQ ID NO:2 as such can be used as the probe.

In obtaining the gene of the invention, the DNA/RNA amplification by PCR [Science, 230, 1350 (1985)] can be used with advantage. Particularly when a full-length cDNA can hardly be obtained from a library, the RACE method [Rapid amplification of cDNA ends; Jikken Igaku (Experimental Medicine), 12(6), 35 (1994)], especially 5'-RACE method [M. A. Frohman, et al., Proc. Natl. Acad. Sci., USA., 8, 8998 (1988)], can be used with advantage.

The primers for use in such PCR methods can be judiciously established with reference to the sequence information on the gene of the invention as disclosed herein and can be synthesized by the routine procedure. The isolation and purification of the amplified DNA/RNA fragment can be carried out in the routine manner as mentioned above, for example by the gel electrophoresis method.

Sequencing of the gene of the invention as obtained in the above manner or various DNA fragments can be made in accordance with the dideoxy method [Proc. Natl. Acad. Sci., USA., 74, 5463 (1977)] or the Maxam and Gilbert method [Methods in Enzymology, 65, 499 (1980)] or more expediently by using a commercial sequencing kit.

For example, with the gene of the invention thus obtained, the expression or non-expression of the gene of the invention in an individual or a given tissue can be specifically detected by utilizing a portion or the whole of the nucleotide sequence of the gene of the invention.

The above detection can be made by the conventional procedures, such as RNA amplification by RT-PCR [reverse transcribed-polymerase chain reaction; E. S. Kawasaki, et al., Amplification of RNA. In PCR Protocol. A Guide to Methods and Applications, Academic Press, Inc., San Diego, 21-27 (1991)], Northern blot analysis [Molecular Cloning, Cold Spring Harbor Lab. (1989)], determination on cellular level by in situ RT-PCR [Nucl. Acids Res., 21, 3159-3166 (1993)] or in situ hybridization, NASBA [nucleic acid sequence-based amplification, Nature, 350, 91-92 (1991)], and the like conventional techniques. The preferred is the RT-PCR detection method.

The primer which is to be used when the PCR method is chosen for the above purpose is not particularly restricted insofar as it is characteristic of the gene of the invention and capable of selective amplification of the particular gene only and can be judiciously established based on the sequence information on the gene of the invention. Usually, one having a partial sequence of the gene of the invention, which is about 10-35 nucleotides long, preferably about 15-30 nucleotides long can be used as the primer.

The gene of the invention, thus, includes the DNA fragment which can be used as a specific primer and/or specific probe for the detection of the LY6H gene of the invention.

The DNA fragment mentioned above can be defined as a polynucleotide which hybridizes with the polynucleotide having the nucleotide sequence shown in SEQ ID NO:2 under stringent conditions. The stringent conditions mentioned above may be the ordinary conditions for primers or probes and, as such, are not particularly restricted. For example, the above-mentioned conditions of 6×SSC, 65° C., overnight or the condition of 50% formamide-4×SSC, 37° C., overnight can be mentioned.

By applying the gene of the invention to the standard genetic engineering technology, the expression product (polypeptide) of the gene or a protein containing it can be easily produced in large quantities and with good reproducibility.

Therefore, the invention further provides a polypeptide having the amino acid sequence encoded by the gene of the invention (the expression product of the invention), a vector harboring the gene of the invention for the production of the polypeptide, a host cell transfected with the vector, and a method of producing the polypeptide of the invention which comprises growing the host cell.

The polypeptide (LY6H protein) having the amino acid sequence shown under SEQ ID NO:1 is a specific embodiment of the polypeptide of the invention. The polypeptide of the invention is not limited to this LY6H protein but includes its homolog. The homolog may be a polypeptide having an amino acid sequence derived from the amino acid sequence shown in SEQ ID NO:1 by the deletion, substitution or addition of one or more amino acids and retaining the same function as the LY6H protein. A specific example of the homolog is the expression product of a homolog of said LY6H gene (the LY6H equivalent gene inclusive of the allele).

Furthermore, the homolog of the LY6H protein of the invention includes proteins having the same activity or function as the polypeptide having the amino acid sequence shown in SEQ ID NO:1 as derived from any of mammals such as equine, sheep, bovine, canine, monkey, cat, bear, etc. and rodents such as rat, mouse and rabbit.

The polypeptide of the invention can be produced by the conventional recombinant DNA technology [e.g. Science, 224, 1431 (1984); Biochem. Biophys. Res. Comm., 130, 692 (1985); Proc. Natl. Acad. Sci., USA., 80, 5990 (1983)] based on the gene sequence information provided by the present invention.

More particularly, the production of said polypeptide is carried out by the procedure comprising constructing a recombinant DNA (expression vector) which permits expression of the gene coding for the desired protein in a host cell, transforming the host cell with the vector, growing the resulting transformant, and harvesting the polypeptide from the culture broth.

The host cell mentioned above may be whichever of a prokaryotic cell and an eukaryotic cell. As the prokaryotic host, *Escherichia coli, Bacillus subtilits* and other common bacteria can be mentioned and preferably cells of *Escherichia coli*, particularly cells of *Escherichia coli* K12, can be employed. The eukaryotic host cell includes cells of vertebrates and yeasts and the former include the monkey cell line COS [Cell, 23: 175 (1981)], Chinese hamster ovarian cells, and the dihydrofolate reductase-defective cells thereof [Proc. Natl. Acad. Sci., USA., 77: 4216 (1980)]. As the latter, yeast cells of the genus *Saccharomyces* can be used with advantage, but these are not exclusive choices.

When prokaryotic cells are used as host cells, an expression plasmid construct prepared by using a vector which is replicatable in the particular host cell and adding a promoter and SD (Shine and Dalgarno) sequence upstream of the gene of the invention so that the gene may be expressed therein as well as an initiation codon (e.g. ATG) necessary for initiation of protein synthesis can be used with advantage. As the vector mentioned above, it is usual to employ plasmids derived from *Escherichia coli*, such as pBR322, pBR325, pUC12, pUC13, etc. However, these are not exclusive choices but various known vectors can be utilized. Examples of the commercial vectors for use in expression systems using *E. coli* include pGEX-4T (Amersham Pharmacia Biotech), pMAL-C2, pMA1-P2 (New England Biolabs), pET21, pET21/lacq (Invitrogen) and pBAD/His (Invitrogen).

As the expression vector for use when cells of a vertebrate are used as host cells, the vector having a promoter upstream of the gene of the invention to be expressed, RNA splice sites, polyadenylation site and a transcription termination sequence is usually employed, and this vector may further have a replication origin where necessary. A specific example of the expression vector is pSV2dhfr harboring an early promoter of SV40 [Mol. Cell. Biol., 1: 854 (1981)]. Aside from the above, various known vectors available commercially can be employed. Examples of the commercial vectors which are used in expression systems using animal cells include vectors for animal cells, such as pEGFP-N, pEGFP-C (CLONTECH), pIND (Invitrogen), pcDNA3.1/His (Invitrogen), etc., and vectors for insect cells, such as pFastBac HT (Gibci BRL), pAcGHLT (PharMingen), pAc5/V5-His, pMT/V5-His and pMT/Bip/V5-his (all Invitrogen).

pAM82 having a promoter for the acid phosphatase gene [Proc. Natl. Acad. Sci., USA., 80:1 (1983)] is a specific example of the expression vector for use when yeast cells are used as host cells. The commercial expression vectors for yeast cells include pPICZ (invitrogen) and pPICZα (Invitrogen).

The promoter is not particularly restricted, either. When a strain of the genus *Escherichia* is used as the host, tryptophan (trp) promoter, lpp promoter, lac promoter, recA promoter, PL/PR promoter, etc. can be utilized with advantage. When the host is a strain of the genus *Bacillus*, SP01 promoter, SP02 promoter, penP promoter, etc. are preferably used. When a yeast is used as the host, pH05 promoter, PGK promoter, GAP promoter, ADH promoter, etc. can be utilized with advantage. The preferred promoter for use when host cells are animal cells include SV40-derived promoters, retrovirus promoters, metallothionein promoter, heat shock promoter, cytomegalovirus promoter, and SRα (promoter.

As the expression vector for the gene of the invention, the conventional fusion protein expression vector can be used with advantage. pGEX (Promega) for the expression of glutathione-S-transferase (GST)-fused proteins is a specific example of the vector.

The polynucleotide sequence wherein the coding sequence for a mature polypeptide assists in the expression and secretion of a polypeptide from host cells includes the secretory sequence, the leader sequence and the marker sequence (hexahistidine tag, histidine tag) used in the purification of a fusion mature polypeptide in the case of bacterial cells, and the hemaglutinin (HA) tag in the case of mammalian cells.

The method of introducing the recombinant DNA (expression vector) into the host cell and the associated transforming method are not particularly restricted but various standardized methods can be utilized.

The transformant obtained can be cultured in the routine manner, whereby the objective protein encoded by the deliberately designed gene according to the invention is expressed and produced (accumulated/secreted) intracellularly, extracellularly or on the cell membrane.

The culture medium to be used can be judiciously selected from among various routine media according to the kind of adopted host cell and the culture is also performed under conditions favoring growth of the host cell.

The resulting recombinant protein (LY6H protein) according to the invention can be optionally isolated and purified by various separation techniques taking advantage of its physical and/or chemical properties, for instance ["Seikagaku Data Book (Biochemical Data Book) II", 1175-1259, First Edition, 1st impression, Jun. 23, 1980, Tokyo Kagaku Dojin K.K.; Biochemistry, 25(25), 8274 (1986); Eur. J. Biochem., 163, 313 (1987), etc.].

Examples of such techniques are the conventional reconstitution method, treatment with a protein precipitating agent (salting-out method), centrifugation, osmotic shock method, sonic disruption, ultrafiltration, various types of chromatography such as molecular sieve chromatography (gel filtration), adsorption chromatography, ion exchange chromatography, affinity chromatography and high performance liquid chromatography (HPLC), dialysis, and combinations of these techniques. The particularly preferred technique includes affinity chromatography using a column to which a specific antibody to the protein of the invention has been coupled.

In designing the objective gene encoding the polypeptide of the invention, the nucleotide sequence of Y6H gene as shown in SEQ ID NO:2 can be utilized with advantage. If desired, this gene can be used after the codons specifying the respective amino acid residues have been judiciously altered. Furthermore, when any amino acid residue or partial sequence of the amino acid sequence encoded by the LY6H gene is to be modified by substitution, deletion or addition, such modifications can be made by the various methods described above, for example by site-specific mutagenesis.

The polypeptide of the invention can be produced by the standard protocol for chemical synthesis according to the amino acid sequence shown in SEQ ID NO:1. The method includes the conventional liquid-phase method and solid-phase method for peptide synthesis.

More particularly, the method for peptide synthesis includes the so-called stepwise elongation method in which the constituent amino acids are coupled one by one for chain extension and the fragment condensation method which comprises synthesizing fragments each consisting of several amino acids beforehand and coupling the fragments together. The synthesis of the protein of the invention can be carried out by whichever of the above two methods.

The method of condensation for use in the above peptide synthesis may also be a conventional one, including the azide process, mixed acid anhydride process, DCC process, active ester process, redox process, DPPA (diphenylphosphoryl azide) process, DCC+additive (1-hydroxybenzotriazole, N-hydroxysuccinamide, N-hydroxy-5-norbornene-2,3-dicarboximide or the like) process and Woodward's reagent process.

The solvent to be used in these processes can also be judiciously selected from among the common solvents well known in the art for use in such peptide-forming condensation reactions. Examples of the solvents include dimethylformamide (DMF), dimethyl sulfoxide (DMSO), hexaphosphoramide, dioxane, tetrahydrofuran (THF), ethyl acetate, etc., and mixtures thereof.

In conducting the peptide synthesizing reactions, the carboxyl group of any amino acid or fragment peptide that should not take part in the reaction can be protected in advance, generally by esterification in the form of a lower alkyl ester such as methyl ester, ethyl ester, tert-butyl ester, etc. or an aralkyl ester such as benzyl ester, p-methoxybenzyl ester, p-nitrobenzyl ester, etc.

Referring to any amino acid having a functional group in its side chain, the hydroxyl group of a tyrosine residue, for instance, may be protected in advance with an acetyl, benzyl, benzyloxycarbonyl, tertiary butyl or other group, although such protection is not necessarily indispensable. Furthermore, the guanidino group of an arginine residue can be protected with a suitable protective group such as nitro, tosyl, p-methoxybenzene-sulfonyl, methylene-2-sulfonyl, benzyloxycarbonyl, isobornyloxycarbonyl, adamantyloxycarboxyl or the like.

The reactions for eliminating such protective groups from the protected amino acids, peptides or the end product protein of the invention can also be carried out in the routine manner, for example by catalytic reduction or a method using liquid ammonia/sodium, hydrogen fluoride, hydrogen bromide, hydrogen chloride, trifluoroacetic acid, acetic acid, formic acid, methane-sulfonic acid or other reagent.

The polypeptide of the invention, thus produced, can be purified as needed by the various techniques mentioned above, such as ion exchange resin chromatography, partition chromatography, gel chromatography, countercurrent distribution and the like methods in routine us in the field of peptide chemistry.

The polypeptide of the invention can be used with advantage as an immunogen for preparation of its specific antibody. By utilizing this immunogen, the antiserum (polyclonal antibody) and the monoclonal antibody can be provided.

The technology of producing antibodies is well known to those skilled in the art and the known procedures can be employed in the present invention [e.g. Zoku Seikagaku Jikken Koza (Experiments in Biochemistry, second series) "Men-eki Seikagaku Kenkyuho (Methods in Immunobiochemistry)", edited by the Biochemical Society of Japan (1986)].

For example, as the immune animal for harvesting the desired antiserum therefrom, the ordinary animals such as rabbit, guinea pig, rat, mouse, chicken, etc. can be arbitrarily selected and the immunization with said immunogen and the collection of blood can also be carried out by the conventional procedures.

Preparation of a monoclonal antibody can also be carried out by the conventional technique which comprises constructing a hybridoma between the plasma cell (immune cell) of an animal immunized with said immunogen and a plasmacytoma cell, selecting clones producing the desired antibody, and cultivating the clones. The immune animal is generally selected in consideration of its compatibility with the plasmacytoma cell to be used for cell fusion and usually the mouse or the rat is used with advantage. The immunization procedure may be the same as used for the preparation of said antiserum and, if desired, the immunization can be made using a conventional adjuvant in combination.

The plasmacytoma cell for use in said hybridization is not particularly restricted, either, but includes various myeloma cells such as p3 (p3/x63-Ag8) [Nature, 256: 495-497 (1975)], p3-U1 [Current Topics in Microbiology and Immunology, 81: 1-7 (1978)], NS-1 [Eur. J. Immunol., 6: 511-519 (1976)], MPC-11 [Cell, 8: 405-415 (1976)], SP2/0 [Nature, 276: 269-271 (1978)], etc., R210 [Nature, 277: 131-133 (1979)] and others in rats, and cells derived therefrom.

The hybridization between said immune cell and said plasmacytoma cell can be effected by the known technology in the presence of a conventional hybridization promoter such as polyethylene glycol (PEG) or Sendai virus (HVJ) and the separation of the objective hybridoma can also be carried out in the known manner [Meth. in Enzymol., 73: 3 (1981); Zoku Seikagaku Jikken Koza (ditto)].

The search for the objective antibody-producing cell clone and the monoclonal antibody preparation can also be carried out in the routine manner. For example, the search for the antibody-producing hybridoma can be made by any of the various techniques in routine use for the detection of antibodies, such as ELISA [Meth. in Enzymol., 70: 419-439 (1980)], plaque method, spot method, agglutination reaction method, Ouchterlony method, radioimmunoassay, and the like, using the protein of the invention as an antigen.

Harvesting of the antibody of the invention from the resulting hybridoma can be achieved by cultivating the hybridoma in the routine manner and recovering the antibody as a culture supernatant or administering the hybridoma to a compatible mammal and recovering the antibody in the form of ascites. The former method is suitable for production of the antibody of high purity, while the latter method is suitable for high-production of the antibody. The antibody thus produced can be further purified by the conventional means such as salting-out, gel filtration, affinity chromatography and the like.

The antibody thus obtained is characterized by its binding affinity for the LY6H protein of the invention and can be used with advantage for the purification of LY6H protein and determination or differentiation of the protein by immunological techniques. Furthermore, since a decreased expression of the gene of the invention has been confirmed in the temporal lobe of the brain of a patient with Alzheimer's disease which is a neurodegenerative disease, this antibody can be utilized in the screening for agonists or antagonists of LY6H protein.

The present invention provides the novel antibody described above, too.

The polypeptide of the invention is useful in the field of medicine as pharmaceutical products containing it as an active ingredient. Therefore, the invention provides a pharmaceutical composition comprising the polypeptide of the invention as an active ingredient.

The usefulness of the polypeptide of the invention in or as said pharmaceutical composition is ascribable to the neuronal survival-supporting action, nerve elongating action, nerve regenerating action, neuroglia-activating action and mnemonic action inherent in this brain-specific polypeptide. Examples of the methods for confirming these actions include the following methods for each action.

1) Neuronal Survival-supporting Action

The following method can be used for quantitating the neuronal survival-supporting action of the polypeptide of the invention. For example, the hippocampus is aseptically isolated from the whole brain of a fetal SD rat and treated with an enzyme, and seeded in a poly-L-lysine (Sigma)-precoated 96-well plate containing 10% fetal calf serum-DMEM at a final concentration of $2 \times 10^5$ cells/cm$^2$.

The cells are grown for 24 hours, at the end of which time the culture medium is changed to 1% N2 Supplement (Gibco)-containing DMEM. Then, the active ingredient polypeptide of the invention is added (the invention group). As control, the polypeptide of the invention which has been heat-treated in a boiling water bath for 5 minutes is added (the boiled protein group).

The cells (culture) in each group as prepared in the above manner are cultured for 72 hours. Then, by performing an MTT [3-(4,5-dimethylthiazol-2-yl)-2,5-diphenyltetrazolium bromide] assay using Promega Cell Titer 96-Well Assay System, the neuronal survival-supporting effect of the polypeptide of the invention on hippocampal neurons can be evaluated.

Similarly, by isolating the ventral midbrain aseptically from the same whole brain of a fetal SD rat as above and carrying out an MTT assay in the same manner as above, the neuronal survival-supporting effect of the polypeptide of the invention on the midbrain neurons can be investigated.

2) Dopaminergic Neuron Survival-supporting Action

As a method of evaluating the neuronal survival-supporting action of the polypeptide of the invention, the following method of quantitating the dopaminergic neuron survival-supporting activity can be mentioned. Thus, the cells (culture) in each group as prepared above under 1) are cultured for 72 hours and, then, fixed with 4% paraformaldehyde-PBS by 15-minute standing at room temperature. Then, using 1% Triton×100/PBS, the culture is passed through a membrane.

To prevent non-specific binding of the antibody, the cells are incubated in 10% goat serum-PBS for 1 hour and, then, using an anti-tyrosine hydroxylase polyclonal antibody (Chemicon, diluted 1000-fold in PBS), further incubated at 4° C. for 16 hours. After removal of the antibody fluid, the cells are washed with PBS and, after addition of peroxidase-labeled dextran polymer-coupled goat anti-rabbit immunoglobulin (Dako), are incubated at room temperature for 1 hour.

Detection of the tyrosine-hydroxylase-positive cells can be made by the color reaction using diaminobenzidine as the substrate. In this manner, the dopaminergic neuronal survival-supporting activity of the polypeptide of the invention can be assayed using the number of tyrosine hydroxylase-positive cells as the indicator.

3) Nerve Elongating Action

The determination of the nerve elongating action (axonal elongation-promoting action) of the polypeptide of the invention can be carried out using PC12 cells [ATCC Accession Number CRL1721; Science, 229, 393-395 (1985)] as follows. Thus, PC12 cells subcultured in modified Dalbecco's MEM (D-MEM) containing 5% of heat-inactivated (56° C., 30 min) horse serum and 10% fetal calf serum (FCS) are transplanted in a collagen-coated plastic petri dish, 35 mm in diameter, at a concentration of $6 \times 10^4$ cells/3 ml. On day 2 after transplantation, the medium was replaced with D-MEM containing a varying concentration of the polypeptide of the invention as well as nerve growth factor (NGF; Wako Pure Chemical Ind.) and FCS and the cultivation is continued in each case. On day 3, morphological changes of the cells are examined with a phase-contrast microscope. By assessing whether the formation of neurites or the promotion of neurite outgrowth is observed in comparison with control, the axonal elongation-promoting potential of the polypeptide of the invention can be evaluated.

4) Neuroglia-activating Action

The neuroglia-activating action can be evaluated, for example by determining the effect of the polypeptide of the invention on the activation of neuroglia by FGF in accordance with the method of Kniss et al. or the method of Bogler et al. [Kniss, D. A., and Burry, R. W., Brain Res., 439, 281-288 (1988); Bogler, O., et al., Proc. Natl. Acad. Sci., USA., 87(16), 6368-6372 (1990)].

5) Mnemonic Action

The mnemonic action can be evaluated, for example, in accordance with the water-maze protocol of Morris [Morris. R. G. M., J. Neurosci. Meth., 11, 47-60 (1984)].

Another evaluation method comprises administering the LY6H protein or an agonist or antagonist of the LY6H protein as selected by a screening to an animal model of Alzheimer's disease such as a mutant β-amyloid precursor protein gene or mutant presenilin 1 gene transgenic mouse [e.g. Nature, 373, 523-527 (1995); Nature Med., 5, 560-564 (1999)] and evaluating the degree of progression of the disease or the degree of nerve degeneration in comparison with a non-treated control group.

Moreover, in order to have the gene expressed in the human temporal lobe (gene therapy), an adenovirus vector [Straus, E. S., Plenum Press New York, 451-496 (1984); Setoguchi, Y., et al., Blood, 84, 2953-2964 (1994)], for instance, is used. Thus, a possible procedure comprises cloning the gene of the invention in an adenovirus vector, culturing it in the stem cell, administering it directly into the temporal lobe or intravenously through a peripheral blood vessel and checking to see whether Alzheimer type dementia or Alzheimer's disease has been improved or its progression inhibited.

The polypeptide as the active ingredient of the pharmaceutical composition of the invention includes its pharmaceutically acceptable salt. Such salt includes nontoxic salts with alkali metals, alkaline earth metals or ammonium, such as salts with sodium, potassium, lithium, calcium, magnesium, barium and ammonium. These salts can be prepared by the conventional methods in the art. Furthermore, said salt includes nontoxic acid addition salts which can be prepared by reacting the active ingredient polypeptide of the invention with suitable organic or inorganic acids. The representative nontoxic acid addition salt includes the hydrochloride, hydrobromide, sulfate, bisulfate, acetate, oxalate, valerate, oleate, laurate, borate, benzoate, lactate, phosphate, p-toluenesulfonate (tosylate), citrate, maleate, fumarate, succinate, tartrate, sulfonate, glycolate, maleate, ascorbate, benzenesulfonate, naphthalenesulfonate, and the like.

The pharmaceutical composition of the invention includes a composition comprising a pharmacologically effective amount of the polypeptide of the invention and a suitable nontoxic pharmaceutical carrier or diluent.

The pharmaceutical carrier which can be used for said pharmaceutical composition (pharmaceutical preparation) includes diluents or excipients which are conventionally utilized according to dosage forms, such as fillers, volume builders, binders, humectants, disintegrators, surfactants, and lubricants. These can be judiciously selected and used according to the unit dosage form of the composition.

The particularly preferred pharmaceutical composition of the invention can be prepared using various additives which can be formulated in ordinary protein preparations, such as the stabilizer, biocide, buffer, isotonizing agent, chelating agent, pH control agent and surfactant.

The stabilizer includes human serum albumin, an L-amino acid, a sugar, and a cellulose derivative, for instance, can be mentioned. These may be used singly or in combination with a surfactant or the like where necessary. The use in combination with a surfactant may lead to a more effective stabilization of the active ingredient in particular.

The L-amino acid is not particularly restricted but may for example be any of glycine, cysteine and glutamic acid.

The sugar is not particularly restricted but includes monosaccharides such as glucose, mannose, galactose, fructose, etc.; sugar alcohols such as mannitol, inositol, xylitol, etc., disaccharides such as sucrose, maltose, lactose, etc.; polysaccharides such as dextran, hydroxypropylstarch, chondroitin sulfate, hyaluronic acid, etc.; and their derivatives.

The surfactant is not particularly restricted, either, but both ionic and nonionic surfactants can be employed. Examples of the surfactant are polyoxyethylene glycol sorbitan alkyl esters, polyoxyethylene alkyl ethers, sorbitan monoacyl esters and fatty acid glycerides.

The cellulose derivative that can be used is not particularly restricted, either, but includes methylcellulose, ethylcellulose, hydroxyethylcellulose, hydroxypropylcellulose, hydroxypropylmethylcellulose, and carboxymethylcellulose sodium.

The level of addition of any of said sugar and other additives can be judiciously selected with reference to the amount in common use. Generally, the sugar is used in a proportion of not less than about 0.0001 mg, preferably within the range of about 0.01 to about 10 mg, per μg of the active ingredient. The surfactant is used generally in a proportion of not less than about 0.00001 mg, preferably within the range of about 0.0001 to about 0.01 mg, per μg of the active ingredient. Human serum albumin, an example of the stabilizer, can be used in a proportion of not less than about 0.0001 mg, preferably within the range of about 0.001 to about 0.1 mg, per μg of the active ingredient. The amount of the amino acid, another example of the stabilizer, can be selected from the range of about 0.001 to about 10 mg per μg of the active ingredient. The level of addition of the cellulose derivative is not less than about 0.00001 mg and is preferably selected from the range of about 0.001 to about 0.1 mg.

The amount of the active ingredient in the pharmaceutical composition of the invention can be liberally selected from a broad range but is generally selected from the range of about 0.00001 to about 70 weight %, preferably about 0.0001 to about 5 weight %.

The pharmaceutical composition of the invention may be further supplemented with a buffer, an isotonizing agent, and a chelating agent. The buffer includes boric acid, phosphoric acid, acetic acid, citric acid, ε-aminocaproic acid, glutamic acid, and the corresponding salts (the alkali metal or alkaline earth metal salts thereof, such as sodium salts, potassium salts, calcium salts and magnesium salts). The isotonizing agent includes sodium chloride, potassium chloride, sugars and glycerol. The chelating agent includes sodium edetate, and citric acid. The level of addition of any of these additives may be within the conventional range.

The pharmaceutical preparation of the invention can be provided in the form of a solution, and in a lyophilized form which can be stored. Such lyophilized preparations can be extemporaneously dissolved in, for example, a buffer inclusive of water, saline or the like at a suitable concentration.

As regards the unit dosage form of the pharmaceutical composition of the invention, various forms can be selected according to the therapeutic objective. The representative form includes solid dosage forms such as tablets, pills, powders, neat powders, granules, capsules, etc. and liquid dosage forms such as solutions, suspensions, emulsions, syrups, elixirs and so on. These dosage forms are generally classified, by route of administration, into oral preparations, parenteral preparations, nasal preparations, vaginal suppositories, rectal suppositories, sublingual tablets, ointments, and others. Each of such dosage forms can be formulated and molded or otherwise prepared by the established pharmaceutical procedure.

For example, tablets can be manufactured using, as said pharmaceutical carrier, any of various excipients such as lactose, sucrose, sodium chloride, glucose, urea, starch, calcium carbonate, kaolin, crystalline cellulose, silicic acid, potassium phosphate, etc.; binders such as water, ethanol, propanol, simple syrup, glucose solution, starch solution, gelatin solution, carboxymethylcellulose, hydroxypropylcellulose, methylcellulose, polyvinylpyrrolidone, etc.; disintegrators such as carboxymethylcellulose sodium, carboxymethylcellulose calcium, low-substitution-degree hydroxypropylcellulose, dried starch, sodium alginate, agar powder, laminaran powder, sodium hydrogen carbonate, calcium carbonate, etc.; surfactants such as polyoxyethylene sorbitan fatty acid esters, sodium lauryl sulfate, monoglycerol stearate, etc.; disintegration inhibitors such as sucrose, stearin, cacao butter, hydrogenated oil, etc.; absorption promoters such as quaternary ammonium bases, sodium lauryl sulfate, etc.; humectants such as glycerol, starch, etc.; adsorbents such as starch, lactose, kaolin, bentonite, colloidal silica, etc.; and lubricants such as purified talc, salts of stearic acid, boric acid powder, polyethylene glycol and so on.

Where necessary, such tablets can be coated with conventional coatings to provide sugar-coated tablets, gelatin-coated tablets, enteric-coated tablets and film-coated tablets. Double-layer or multi-layer tablets may also be employed.

The pharmaceutical carrier which can be used for the production of pills includes various excipients such as glucose, lactose, starch, cacao butter, hydrogenated vegetable oil, kaoline, talc, etc.; binders such as gum arabic powder, tragacanth powder, gelatin, ethanol, etc.; and disintegrators such as laminaran and agar.

The capsules can be generally manufactured in the conventional manner by blending the active ingredient of the invention with the pharmaceutical carrier or carriers and filling the resulting composition into hard gelatin capsule shells, soft capsule shells or the like.

The liquid preparation for oral administration includes pharmaceutically acceptable solutions, emulsions, suspensions, syrups, elixirs, etc. as formulated with routine inert diluents, such as water, and these dosage forms may contain a wetting agent, an emulsifier, a suspending agent and/or other auxiliary additives. These can be manufactured by the established pharmaceutical procedures.

The liquid preparation for parenteral administration, inclusive of sterile aqueous and non-aqueous solutions, emulsions and suspension, can be prepared using such diluents as water, ethyl alcohol, propylene glycol, polyethylene glycol, ethoxylated isostearyl alcohol, polyoxylated isostearyl alcohol, polyoxyethylene sorbitan fatty acid esters, and vegetable oils such as olive oil. In addition, injectable organic esters, such as ethyl oleate, may be formulated. Furthermore, any of the conventional solubilizers, buffers, wetting agents, emulsifiers, suspending agents, preservatives, dispersants, etc. can also be added.

The above various pharmaceutical dosage forms are sterilized in the routine manner. This sterilization can be achieved by filtration through a bacterial filter, formulation of a biocide, irradiation, or a heat treatment. Furthermore, these may be provided in the form of sterile solid compositions which can be extemporaneously dissolved in sterile water or a suitable sterilizable medium.

For the manufacture of dosage forms for rectal or vaginal administration, such pharmaceutical carriers as polyethylene glycol, cacao butter, higher alcohols, higher alcohol esters, gelatin, semisynthetic glycerides, etc. can be employed.

Ointments such as pastes, creams and gels can be prepared using a diluent such as white petrolatum, paraffin, glycerol, cellulose derivatives, propylene glycol, polyethylene glycol, silicone, bentonite, and vegetable oils such as olive oil.

Compositions for transnasal or sublingual administration can be prepared in the routine manner using a well-known standard excipient.

Where necessary, those pharmaceutical preparations of the invention may be supplemented with coloring agents, preservatives, perfumes, flavoring agents, sweeteners, and other drugs.

The method for administration of such pharmaceutical preparations is not particularly restricted but can be selected according to the specific dosage form, patient's age, sex and other factors, severity of illness, and other variables. For example, tablets, pills, solutions, suspensions, emulsions, granules and capsules are administered orally, while parenteral products are administered intravenously, either alone or in admixture with the conventional glucose, amino acid or other infusion, or, where necessary, administered alone intramuscularly, intradermally, subcutaneously or intraperitoneally. The rectal suppositories are administered into the rectum; the vaginal suppositories are administered into the vagina; the nasal preparations are administered into the nostrils, the sublingual preparations are administered buccally, and the ointments are administered topically for transdermal drug delivery.

The dosage for any of the above pharmaceutical preparations is not particularly restricted but can be judiciously selected from a broad range according to the expected therapeutic effect, administration method, duration of treatment, patient background such as age and sex, and other factors. Generally, the recommended usual dosage of the active ingredient is about 0.01 μg-10 mg/day, preferably about 0.1 μg-1 mg/day, per kg of the patient's body weight. The above dose may be administered once a day or in 2 or more divided doses.

Furthermore, as pointed out in the working example to be presented later herein, the expression of the gene of the invention has been abolished or decreased in the temporal lobe of patients with Alzheimer's disease. Therefore, by constructing an arbitrary expression vector harboring the whole or part of the gene of the invention and introducing the expression vector into the temporal lobe tissue for forced expression of the gene in the tissue, neurodegenerative changes inclusive of an excessive atrophy of neurons in the temporal lobe may be inhibited and, hence, the progression of Alzheimer's disease may be arrested. Therefore, the present invention further provides a pharmaceutical composition for gene therapy (gene therapeutic agent) which is possessed of such a neurodegeneration-inhibitory action.

The present invention further provides the above expression vector or vector for gene therapy, cells transfected with the gene of the invention through the introduction of said vector, and a pharmaceutical composition for gene therapy which comprises any of the above as the active component.

The gene therapy using said gene therapeutic agent is performed by administering at least one member selected from the group consisting of the vector for introduction and expression of the gene of the invention and cells transfected with the gene of the invention through the introduction of said vector into the brain neurons or temporal lobe tissue of a patient with neurodegenerative disease. By such a procedure, neurodegenerative changes in such tissue can be inhibited and symptoms of Alzheimer's disease, Alzheimer type dementia, Parkinson's disease, brain ischemia, etc. can be alleviated.

The gene therapy is now described in further detail. In the following execution of a gene therapy, the routine chemical, molecular biological, microbiological, recombinant DNA, genetic, and immunological techniques can be employed unless otherwise specified. These techniques are described in, inter alia, Maniatis, T., et al., Molecular Cloning: A laboratory manual (Cold Spring Harbor Laboratory), Cold Spring Harbor, N.Y. (1982)), Sambrook, J., et al., Molecular Cloning: A laboratory manual, 2nd Ed. (Cold Spring harbor Laboratory), Cold Spring harbor, N.Y. (1981)), Ausbel, F. M., et al., Current Protocols in Molecular Biology, John Wiley and Sons, New York (1992)), Glover, D., DNA Cloning, I and II (Oxford Press (1985)), Anand, Techniques for the Analysis of Complx Genomes (Academic Press (1992), Guthrie, G., et al., Guide to Yeast Genetics and Molecular Biology (Academic Press (1991)), and Fink, et al., Hum. Gene Ther., 3, 11-19 (1992).

The gene therapy can be carried out using a gene therapy vector harboring the whole or part of the gene of the invention or cells transfected with the gene of the invention through the introduction of said vector. This gene therapy may for example be a method of supplying the LY6H gene or its function to cells in which said gene has not been expressed. By such gene therapy, neurodegeneration around the receptor cell/target cell is inhibited.

The gene of the invention or a fragment of the gene can be introduced into cells by means of a vector adapted to maintain the gene extrachromosomally. In such cases, the particular gene can be caused to be expressed by the cells from an extrachromosomal position. Moreover, when the LY6H gene is to be expressed by introducing a fragment of the gene into the temporal lobe site of the brain nervous system where no expression of the gene is found, the particular fragment of the gene may be a fragment encoding a part of LY6H protein which is necessary for the survival or non-tumorigenic growth of cells.

The gene transfer vector may be any of various known vectors in which the gene of the invention has been subcloned as will be described later herein.

The introduction of the gene transfer vector into the target cell can be easily effected by the established technology of introducing DNA into various cells which is already known to those skilled in the art, such as electroporation, calcium phosphate transfection (coprecipitation), virus transduction and other techniques. The cells transfected with the gene of the invention can be utilized as a drug for neurodegenerative disorders of the brain, inclusive of an inhibitor of premature atrophy of the brain nervous system, or as models for therapeutic research.

As mentioned above, the gene or gene fragment of the invention as introduced by the gene therapy according to the invention increases the expression of the corresponding gene product in the brain nerve or surrounding tissue to thereby inhibit atrophy of the brain nerve in the tissue expressing the gene. Such gene therapy can be applied with advantage to the brain neuronal tissue where the expression of LY6H gene or the LY6H protein has been abolished as well as to the brain neuronal tissue where the level of expression of said gene has been depressed.

The gene therapy according to the present invention is performed as follows. First, a screening is carried out for candidate patients for the gene therapy by recording a computer tomogram (CT) with the scanning position fixed to the temporal lobe of the patient with Alzheimer type dementia or Alzheimer's disease to check for atrophy of the temporal lobe or progression of the atrophy.

Then, to achieve expression of the gene of the invention, the intracellular LY6HmRNA is created in the target cell and its translation is promoted to accelerate expression of the LY6H gene. For this purpose, preferably a sense oligonucleotide corresponding to the mRNA of the gene is produced and supplied to the target cell. By providing the cell with the activity to promote expression of the LY6H gene by the above gene therapy, the neurodegenerative change in the brain receptor cell/target cell can be inhibited.

According to the above gene therapy using said sense oligonucleotide, the objective inhibition of neurodegenerative change of the brain and consequent alleviation or arrest of progression of neurodegenerative symptoms may be successfully attained by subcloning the LY6H gene into a retrovirus, adenovirus or AAV-derived vector and infecting the target brain nerve cells with the vector to thereby cause expression of the sense oligonucleotide.

When a sense oligonucleotide of the gene of the invention is introduced into the cerebral neuron or tissue to increase the expression of LY6H protein, the sense oligonucleotide need not be the full-length nucleotide of the LY6H gene but may be the modification product insofar as it retains a function substantially identical to the function of the parent gene and promotes expression of the LY6H gene or a fragment gene comprising a partial sequence retaining said function.

Vectors which can be used for introducing an objective gene for both DNA recombination and extrachromosomal gene maintenance are already known in the art and any of such known vectors can be used in the practice of the invention. For example, a virus or plasmid vector which includes a copy of LY6H gene sense oligonucleotide ligated to the expression control element and is capable of expressing the sense-oligonucleotide product in the target cell can be used as such vectors.

Any of the expression vectors mentioned above can be usually employed but the preferred are vectors constructed by using any of the vectors disclosed in U.S. Pat. No. 5,252,479 and WO 93/07282 (specifically pWP-7A, pWP-19, pWU-1, pWP-8A, pWP-21 and/or pRSVL) or the pRC/CMV (Invitrogen) as the source vector. The still more preferred are the various virus vectors described later herein.

As the promoter for use in the vector for gene therapy, those promoters, which are intrinsic to the affected tissues to be treated in various diseases, are preferably employed. Examples of the promoters are albumin, α-fetoprotein, α1-antitrypsin, transferrin, and transthyretin for the liver, and carbonic anhydrase I and carcinoembryonic antigen for the colon. When the affected tissues are the uterus and placenta, estrogen, aromatase, cytochrome P450, cholesterol side-chain-cleaving enzyme P450, and 17α-hydroxylase P450 can be exemplified.

For the prostate, prostate-specific antigens, gp91-fox gene, and prostate-specific kallikrein can be exemplified. For the breast, erb-B2, erb-B3, β-casein, β-lactoglobin, and whey protein can be exemplified. For the lung, surfactant protein C, and uroglobulin can be exemplified. For the skin, K-14-keratin, human keratin 1 or 6, and leucline can be exemplified. For the brain, glial fibrillary acidic protein, mature astrocyte-specific protein, myelin, tyrosine hydroxylase pancreatic villin, glucagon, and Langerhans islet amyloid polypeptide can be exemplified. For the thyroid, thyroglobulin, and calcitonin can be exemplified. For the bone, α1 collagen, osteocalcin, and bone sialoglycoprotein can be exemplified. For the kidney, renin, liver/bone/kidney alkaline phosphatase, and erythropoietin can be exemplified, and for the pancreas, amylase, and PAP1 can be exemplified.

Furthermore, in the production of a vector for introduction of a sense oligonucleotide, the sense oligonucleotide to be introduced (one having a full-length or partial sequence corresponding to the sequence of the gene of the invention) can be easily prepared and acquired by the standard genetic engineering techniques based on the nucleotide sequence information on the gene of the invention as described hereinbefore.

The transfer of such a vector for introduction of a sense oligonucleotide into cells can be carried out by various techniques already known in the art, such as electroporation, calcium phosphate transfection (coprecipitation), virus transduction and the like. The cells transfected with said sense oligonucleotide, as such and in an isolated form, have a brain neurodegeneration-inhibitory action so that they can be used as a drug, or a therapeutic research model, for the inhibition or arrest of progression of neurodegenerative lesions as well.

In gene therapy, the above vector for introduction of a sense oligonucleotide can be injected either topically into the temporal lobe or surrounding region of the patient or systemically. Furthermore, it may be cultured together with stem cells and, then, administered by local or systemic injection. By such administration, the vector can be introduced into the nerve cells of the patient's brain. In the event the transduced gene is not permanently taken up in the chromosome of each target cell, the administration may be repeated periodically.

The method for gene therapy according to the invention includes both the in vivo technique which comprises administering a construct for introduction of said sense oligonucleotide (a sense oligonucleotide transfer vector) directly into the body and the ex vivo technique which comprises transferring the gene into cultured stem cells and, after culturing, transplanting or otherwise introducing the cells into the patient's body. A gene therapy comprising introducing said sense oligonucleotide directly into the cell is also feasible.

The target cells into which the sense oligonucleotide of the gene of the invention is to be introduced can be judiciously selected according to the object of gene therapy (treatment). For example, the target cells include brain neurons and brain nerve tissues as well as lymphocytes, fibroblasts, hepatocytes and hemopoietic cells.

The method of introducing the sense oligonucleotide in the above gene therapy includes a viral introduction technique and a non-viral introduction technique.

As to the viral introduction technique, in consideration of the fact that the sense oligonucleotide to be transferred is a foreign substance which is expressed especially in the normal brain cells, the method using a retrovirus vector, for instance, can be exemplified. Other virus vectors which can be used include the adenovirus vector, HIV (human immunodeficiency virus) vector, adeno-associated virus (AAV) vector, herpes virus vector, herpes simplex virus (HSV) vector, and Epstein-Barr virus (EBV) vector.

The method of constructing a virus vector for transfer of a sense oligonucleotide and the method for transfer of the sense oligonucleotide to the target cell or target tissue are now specifically described.

The retrovirus vector system consists of a virus vector and a helper cell (packaging cell). The helper cell means a cell which has expressed genes encoding the structural protein gag (structural protein within the virus particle), pol (reverse transcriptase), env (coat protein), etc. of a retrovirus but which has not formed virus particles. On the other hand, the virus vector has the packaging signal and LTR (long terminal repeats) but lacks structural genes, such as gag, pol, env, etc., which are necessary for virus replication. The packaging signal is a sequence which functions as a tag in the assembly of a virus particle. Selective genes (neo, hyg) and the object sense oligonucleotide ligated in the cloning site are inserted in lieu of the virus genes. In order that a high titer of virus particles may be obtained, it is important to use an insert as short as possible, provide a broad packaging signal including a part of the gag gene, and use care not to leave ATG of the gag gene.

As the vector DNA harboring the object sense oligonucleotide is transferred to the helper cell, the vector genomic RNA is packaged by the virus structural protein formed by the helper cell, whereby virus particles are formed and secreted. The virus particle as a recombinant virus infects the target cell and, as a result, the DNA sequence reverse-transcribed from the virus genomic RNA is integrated into the cell nucleus so that the sense gene inserted in the vector is expressed.

It may be employed a technique using a fibronectin fragment containing the cell adhesion domain, heparin-binding site and conjugating segment [Hanenberg, H., et al., Exp. Hemat., 23, 747 (1995)], for enhancing the efficiency of transfer of the object gene.

An example of the retrovirus vector for use in the above retrovirus vector system is the retrovirus derived from mouse leukemia virus [McLachlin, J. R., et al., Proc. Natl. Acad. Res. Molec. Biol., 38, 91-135 (1990)].

The method using an adenovirus vector is now described in detail. The adenovirus vector can be constructed in accordance with the methods described in Berkner, K. L., Curr. Topics Microbiol. Immunol., 158, 39-66 (1992), Setoguchi, Y., et al., Blood, 84, 2946-2953 (1994), Kanegae, H. et al. [Jikken Igaku (Experimental Medicine), 12, 28-34 (1994)] and Ketner, G. et al., Proc. Natl. Acad. Sci., USA., 91, 6186-6190 (1994).

For example, to construct a non-proliferative adenovirus vector, the early region E1 and/or E3 of the adenovirus is excised in the first place. Then, a plasmid vector containing the desired foreign gene expression unit (which consists of the sense oligonucleotide to be transferred, the promoter for transcription of said sense oligonucleotide, Poly A for insuring the stability of the transcribed gene) and a part of the adenovirus genomic DNA and a plasmid containing the adenovirus genome are used to cotransfect the 293 cell, for instance. As a homologous recombination is thus caused to take place between them for substitution of the gene expression unit for E1, a nonproliferative adenovirus vector is obtained as a vector harboring the object sense oligonucleotide. A 3'-end adenovirus vector with a terminal protein added can also be constructed by ligating the adenovirus genomic DNA in a cosmid vector. Furthermore, the YAC vector may also be utilized for the construction of an adenovirus vector.

Production of an adeno-associated virus (AAV) vector is now described briefly. AAV was discovered as a small virus contaminating adenovirus culture systems. As to this virus, the existence of the genus *Parvovirus* capable of autonomous proliferation within the host cell without requiring a helper virus for virus replication and the genus *Dependovirus* which requires a helper virus has been identified. This AAV has a broad host range and is one of the common viruses infecting various kinds of cells. The virus genome is a linear single-stranded DNA consisting of 4680 nucleotides, with the 145 nucleotides at both ends having a characteristic sequence known as ITR (inverted terminal repeat). This ITR region functions as the replication origin and plays the role of a primer. This ITR is also essential to packaging for virus particles and integration of AAV into the chromosome DNA of the host cell. In regard of the virus protein, the left-half of the genome codes for the nonstructural protein, that is the regulatory protein Rep which controls replication and transcription.

Construction of the recombinant AAV can be carried out by utilizing the property of AAV to become integrated into the chromosome DNA, whereby the desired gene transfer vector can be prepared. This method may be described in detail as follows. First, a plasmid (AAV vector plasmid) retaining the ITRs at 5'- and 3'-ends of a wild-type AVV and harboring the sense oligonucleotide to be transferred as interposed therebetween is constructed. The virus protein necessary for virus replication and formation of virus particles is supplied from a separate helper plasmid. It is necessary to insure that no common nucleotide sequence will exist between the two plasmids so that a wild-type virus will not appear on DNA recombination. Thereafter, the two plasmids are transferred into the 293 cell by transfection, for example, and, further, the cells are infected with an adenovirus as the helper virus (when the 293 cell is used, this adenovirus may be a non-proliferative one), whereby the desired non-proliferative recombinant AAV is produced. Since this recombinant AAV is present in the nucleus, the cells are subjected to freeze-thawing and recovered and the contaminant adenovirus is inactivated by heating at 56° C. Then, where necessary, the recombinant AAV is separated and concentrated by ultracentrifugation using cesium chloride. In this manner, the desired recombinant AAV for gene transfer can be obtained.

Production of an EBV vector can be carried out by the method of Shimidzu et al. [Shimidzu, N., SAIBO KOUGAKU (Cell Technology, 14(3), 280-287 (1995)].

Production of the EBV vector for transfer of the sense oligonucleotide according to the invention is now described briefly. EB virus (Epstein-Barr virus) is a virus of the family *Herpesviridae,* which was first isolated by Epstein and coworkers from cultured cells derived from Burkitt lymphoma [Kieff, E. and Liebowitz, D.: Virology, 2nd ed. Raven Press, New York, 1990, pp. 1889-1920]. This EBV has cell-transforming activity and in order to use it as a vector for gene transfer, it is necessary to prepare a virus defected of this transforming activity. This can be done as follows.

Thus, first of all, the EBV genome in the vicinity of the target DNA in which the desired foreign gene is to be inserted is cloned. Then, a DNA fragment of the foreign gene and a drug-resistant gene are inserted to construct a vector for preparation of a recombinant virus. Then, the vector for preparation of a recombinant virus as excized with a suitable restriction enzyme is transfected to EBV-positive Akata cells. The recombinant virus formed by homologous recombination is recovered, together with the wild type Akata EBV, through stimulation of virus production by anti-surface immunoglobulin treatment. The recombinant virus is infected to EBV-negative Akata cells and, in the presence of a drug, resistant clones are selected, whereby Akata cells infected exclusively with the recombinant virus free of wild type EBV can be obtained. Further, by inducing viral activity in the recombinant virus-infected Akata cells, the objective recombinant virus vector can be produced in quantities.

The method of introducing the object gene into the target cell or target tissue in the gene therapy of the invention includes the following representative two methods.

The first method comprises harvesting the target cells from a patient to be treated, growing the cells ex vivo, for example under addition of interleukin-2 (IL-2) or the like, to transfer the objective sense oligonucleotide harbored in the retrovirus vector, and retransplanting the resulting cells (ex vivo method). This method is suitable for the therapy of genetic diseases caused by defective genes and cancer, for instance.

The second method is a method for direct gene transfer which comprises injecting the object sense oligonucleotide directly into the patient's body or the target site such as the cerebral tissue (direct method).

More particularly, the first method can be carried out in the following manner, for instance. Thus, the mononuclear cells, such as stem cells, harvested from the patient are fractionally separated from monocytes using a blood sorter and cultured in the presence of IL-2 in a suitable medium such as AIM-V medium for about 72 hours, followed by addition of the vector harboring the sense oligonucleotide to be introduced. For enhancing the efficiency of transfer of the sense oligonucleotide, the cells may be grown in the presence of protamine at 32° C. for 1 hour, centrifuged at 2500 ppm, and then cultured under 10% carbon dioxide gas at 37° C. for 24 hours. After this procedure is repeated a few times, the cells are further cultured in the presence of IL-2 in, for example, AIM-V medium for 48 hours and then washed with saline. The viable cells are counted and the efficiency of introduction of the sense oligonucleotide is evaluated by said in situ PCR or, when the object is enzymatic activity, assaying the degree of the enzymatic activity.

The safety checks such as culture of bacteria and fungi in cultured cells, check for the presence or absence of mycoplasma infection, search for endotoxin, etc. are carried out to confirm safety. Thereafter, the cultured cells transformed with the predicted effective dose of the sense oligonucleotide are returned to the patient by intravenous drip injection. The above procedure is repeated at intervals of several weeks or a few months to consummate the gene therapy.

The dosage of the virus vector is judiciously selected according to the target cell. The usually preferred dose may for example be $1 \times 10^3$ cfu-$1 \times 10^8$ cfu in terms of virus titer per $1 \times 10^8$ target cells.

It can be adopted an alternative version of the above first method that comprises co-cultivating the virus-producer cells having the retrovirus vector harboring the object sense oligonucleotide and the patient's cells to thereby introduce the sense oligonucleotide into the target cells.

In carrying out the second method (direct method) for gene therapy, it is particularly preferable to perform a preliminary experiment ex vivo to check whether the objective sense oligonucleotide can be actually introduced by the gene transfer method by carrying out PCR of the vector gene cDNA or in situ PCR or check whether the desired therapeutic effect, for example elevation of a specific activity or the growth or inhibition of growth of the target cell can be actually achieved by introduction of the objective sense oligonucleotide. Moreover, when a virus vector is used, it is, of course, of great importance to confirm the safety of introduction of the sense oligonucleotide in gene therapy by performing a PCR search for proliferative retrovirus and the like, determining the reverse transcriptase activity, or monitoring the coat protein (env) gene by the RCR technique.

The gene therapy of the invention in Alzheimer's disease, Alzheimer type dementia or Parkinson's disease may for example be a therapy of neurodegenerative disease which comprises harvesting stem cells or brain nerve cells from the patient, establishing a cultured cell line by enzymatic treatment or the like, introducing the object sense oligonucleotide into the target brain nerve cells utilizing AAV or the like, carrying out a screening with G418 cells, measuring the amount of expression of IL-12 or the like in vivo, giving a radiation treatment, and inoculating the cells into the patient's brain tissue or the temporal lobe site.

The present invention further provides a pharmaceutical composition or preparation (a gene therapeutic agent) comprising a sense oligonucleotide transfer vector of the invention or a cell line transformed with the sense oligonucleotide as an active ingredient in a pharmacologically effective amount in combination with a suitable nontoxic pharmaceutical carrier or diluent.

The pharmaceutical carrier that can be utilized in the pharmaceutical composition (pharmaceutical preparation) of the invention includes those diluents or excipients, e.g. fillers, volume builders, binders, humectants, disintegrators, surfactants, lubricants, etc., which are usually employed depending on the mode of use of such a composition, and these can be selectively used according to the contemplated unit dosage form of the preparation.

The unit dosage form of the pharmaceutical preparation of the invention may be the same as mentioned for the polypeptide preparation of the invention, and a suitable one can be judiciously selected according to the therapeutic objective.

The therapeutic and prophylactic method for neurodegenerative disease according to the invention is now described in detail.

The present invention provides a method for therapy of neurodegenerative diseases, such as Alzheimer's disease, Alzheimer type dementia, brain ischemia, Parkinson's disease, and like diseases in which either an excess or a shortage of the LY6H polypeptide is involved. When LY6H activity is excessive, several approaches can be taken. The first method comprises administering an inhibitor compound (antagonist) in an effective amount to inhibit the function of LY6H polypeptide by blocking its binding to a ligand, substrate, receptor, enzyme or the like or inhibiting a secondary signal in combination with a pharmaceutically acceptable carrier to thereby improve an abnormal state. An alternative method comprises administering a soluble-form LY6H polypeptide capable of binding to a ligand, substrate, enzyme, receptor or the like in competition with the endogenous LY6H. A typical example of such competitive substance includes a fragment of LY6H polypeptide. In another method, a soluble-form LY6H polypeptide capable of binding to a ligand in competition with endogenous LY6H can be administered. A typical example of such competitive substance includes a fragment of LY6H polypeptide.

In a still another method, expression of the gene coding for endogenous LY6H polypeptide can be inhibited by applying a gene expression inhibition technique to the LY6H gene product. The known technique of this kind includes the use of an internally generated or separately administered antisense sequence [e.g. Oligodeoxynucleotides as Antisense Inhibitors of Gene Expression, CRC Press, Boca Raton, Fla. (1988), O'Connor, J. Neurochem 56: 560 (1991)]. As an alternative method, an oligonucleotide capable of forming a triple helix with the gene can be supplied [e.g. Lee et al., Nucleic Acids Res., 6: 3073 (1979); Cooney et al., Science, 241: 456 (1988); Dervan et al., Science, 251: 1360 (1991)]. These oligomers can be administered as such or related oligomers may be caused to be expressed in vivo.

For the therapy of abnormal symptoms related to an under-expression of LY6H and its activity, several methods can be utilized. The first method comprises administering a compound capable of activating LY6H (agonist) in a therapeutically effective amount together with a pharmaceutically acceptable carrier to a subject to thereby improve the abnormal symptoms. In another method, the endogenous production of LY6H by related cells in the subject can be actuated by gene therapy. For example, the polynucleotide of the present invention may be manipulated so as to be expressed with a defective retrovirus vector as mentioned hereinbefore. Then, this retrovirus expression construct is isolated and introduced into packaging cells transduced with a retrovirus plasmid vector harboring the RNA encoding the polypeptide of the invention so that the packaging cells will form infective virus particles containing the object gene. These producer cells are administered to the subject for in vivo manipulation of the cells so that the polypeptide may be expressed in vivo. For an overview of gene therapy, reference may be made to Human Molecular Genetics, T. Strachan and A. P. Read, BIOS Scientific Publishers Ltd. (1996), Chapter 20—Gene Therapy and Other Molecular Genetic-based Therapeutic Approaches, inclusive of the specific references cited therein. An alternative method comprises administering a therapeutic dose of LY6H polypeptide in combination with a suitable pharmaceutical carrier.

The cells may for example be formulated in phosphate-buffered saline (pH 7.4), Ringer's solution or an intracellular composition injection or in such a dosage form as can be administered in combination with a substance conducive to an enhanced gene transfer efficiency, such as protamine.

The method of administering the above pharmaceutical preparation is not particularly restricted but a suitable regimen can be established according to the particular dosage form, the patient's age, sex and other factors, the severity of illness, and the like.

The amount of the active ingredient to be incorporated in the pharmaceutical preparation and the dosage are not particularly restricted but each can be liberally selected from a broad range according to the expected therapeutic benefit, method of administration, duration of treatment, patient background inclusive of age and sex, and other variables.

Generally, the dosage of the retrovirus vector harboring the sense oligonucleotide as a pharmaceutical preparation may for example be about $1 \times 10^3$ pfu through $1 \times 10^{15}$ pfu in terms of retrovirus titer per kilogram body weight per day.

In the case of cells carrying the sense oligonucleotide for introduction, the dosage can be properly selected from the range of about $1 \times 10^4$ cells/body through $1 \times 10^{15}$ cells/body.

The above preparation can be administered once a day or in a few divided doses a day, or even intermittently at intervals of 1 or several weeks. Preferably, a substance conducive to an enhanced gene transfer efficiency, such as protamine, or a preparation containing the same can be administered in combination.

When the gene therapy according to the invention is applied to the therapy of a neurodegenerative disease, it can be performed in a suitable combination with other gene therapies (conjunctive gene therapy) or in combination with a pharmacotherapy utilizing an acetylcholinesterase inhibitor or the like and/or a rehabilitation therapy. The gene therapy of the invention can be performed with reference to the NIH guidelines, inclusive of its safety aspect [Recombinant DNA Advisory Committee, Human Gene Therapy, 4, 365-389 (1993)].

Furthermore, in accordance with the invention, for the purpose of detecting the presence of LY6H gene, it is possible to prepare a biological sample such as blood or serum, optionally extract the nucleic acid, and analyzing it for LY6H gene.

The method of detecting the gene may comprise preparing a DNA fragment of the gene of the invention and design it so that it may be used in the screening for LY6H gene and/or its amplification. More specifically, it is possible to construct a DNA fragment having the properties of a probe for plaque hybridization, colony hybridization, Southern blotting, Northern blotting, etc. or a probe for the preparation of a full-length or partial DNA of the gene of the invention as amplified by a polymerase chain reaction (PCR) which amplifies a nucleotide sequence with a polymerase. For this purpose, a primer having the same sequence as LY6H gene is first prepared. Then, this primer is reacted, as a probe for screening, with a biological sample (nucleic acid sample) to check for the presence of the particular LY6H gene sequence. The nucleic acid sample may be prepared by any of various techniques facilitating detection of the target sequence, such as denaturation, restriction enzyme digestion, electrophoresis or dot blotting.

As the method for said screening, the use of a PCR technique is particularly preferred from sensitivity points of view, and this technique is not particularly restricted inasmuch as a fragment of the gene of the invention is used as a primer. Thus, It can be utilized that any of the hitherto-known techniques [Science, 230, 1350-1354 (1985)] and the modified versions of PCR which have been developed of late or will be developed in the future [Sakaki, Yoshiyuki et al. (ed.), Jikken Igaku (Experimental Medicine), Supplement 8(9) (1990), Yodosha; Protein, Nucleic Acid, Enzyme: Special Supplement, Kyoritsu Shuppan, 35(7) (1990)].

The DNA fragment for use as the primer is a chemically synthesized oligo-DNA, and such oligo-DNA can be synthesized using an automated DNA synthesizer or the like, for example Pharmacia LKB Gene Assembler Plus (Pharmacia). The preferred length of the primer (sense primer or antisense primer) to be synthesized may for example be about 10-30 nucleotides. The probe for us in said screening is usually a labeled probe but may be an unlabeled one, or the detection may be made according to specific binding to a directly or indirectly labeled ligand. The suitable label and the method of labeling the probe or ligand belong to the prior art. Thus, the prior art label includes radioisotopes, biotin, fluorescent groups, chemiluminescent groups, enzymes, antibodies, etc., which can be taken up through known procedures such as nick translation, random priming and kinase treatment.

The PCR technique to be used for detection may for example be RT-PCR but various modifications of the technique which are in routine use in the art can be utilized.

Furthermore, the above assay method can be expediently carried out by utilizing a reagent kit for detecting an LY6H gene in samples.

Therefore, the present invention provides an LY6H gene detection reagent kit comprising a DNA fragment of the gene of the invention.

This reagent kit comprises at least a DNA fragment which hybridizes with a part or the whole of the nucleotide sequence shown in SEQ ID NO:2 or its complementary nucleotide sequence as an essential component and may optionally contain other components such as a labeling agent and PCR reagents (for example, Taq DNA polymerase, deoxynucleotide triphosphates, primers, etc.).

The labeling agent may be a radioisotope or a chemical modifier such as a fluorescent substance but the DNA fragment as such may have been conjugated with such a labeling agent. This reagent kit may further contain a suitable reaction solvent or diluent, standard antibody, buffer, wash solution, reaction stopper solution, etc. which make an assay easier to perform.

The present invention in a further aspect provides a method for diagnosis of neurodegenerative diseases which comprises using the above assay method and a diagnostic agent or diagnostic reagent kit for use in practicing said method.

By the direct or indirect sequencing of the LY6H genes obtained from test samples by utilizing the above method, it is possible to find new LY6H gene-related genes having high homology to the wild-type LY6H gene.

Therefore, the present invention further provides a method of screening for human LY6H gene-related genes in samples which comprises performing said assay and sequencing of the LY6H genes contained in test samples.

The wild-type LY6H and/or mutant LY6H can be determined by utilizing the protein encoded by the human LY6H gene of the invention (a polypeptide having the amino acid sequence shown in SEQ ID NO:1), a polypeptide having an amino acid sequence derived from the sequence shown in SEQ ID NO:1 by the deletion, substitution or addition of 1 or a plurality of amino acids, a fragment of either of them, or an antibody to any of such proteins.

Therefore, the invention provides a method of determining an anti-wild-type LY6H and/or mutant LY6H antibody or a method of determining the antigen. By this method, the degree of impairment of the brain nerve can be detected from a change in wild-type LY6H (polypeptide) Such changes can be detected by the sequencing of LY6H by the well-established technology described hereinabove, more preferably by detecting differences in the LY6H polypeptide or the presence or absence of LY6H polypeptide by the use of said antibody (polyclonal or monoclonal antibody).

The following is a specific example of determination of said wild-type and/or mutant LY6H. The anti-LY6H antibody can be used to immunoprecipitate LY6H polypeptide from a solution containing a biological sample obtained from a human body, such as blood or serum or can be reacted with the LY6H polypeptide on polyacrylamide gel of Western blot or immunoblot. The LY6H polypeptide in a paraffin section or frozen tissue specimen can be detected by an immunohistochemical technique using the anti-LY6H antibody. The antibody production and purification technology are well known in the art and suitable techniques can be selectively employed.

The preferred technology relevant to the detection of a wild-type LY6H or a mutant thereof includes enzyme-linked immunosorbent assay (ELISA), radioimmunoassay (RIA), immunoradiometric assay (IRMA) and immunoenzymometric assay (IEMA) with a sandwich technique using a monoclonal antibody and/or a polyclonal antibody.

The invention further provides an LY6H ligand or an LY6H receptor existing in a cell membrane fraction or on a cell surface and having binding affinity for LY6H polypeptide. The LY6H receptor can be obtained by conjugating a labeled LY6H polypeptide in a biological sample containing a cell membrane fraction, extracting, isolating and purifying the conjugation product and identifying the amino acid sequence of the isolated product. The procedure for preparation and the method of sequencing this LY6H receptor polypeptide is obvious to one skilled in the art.

Furthermore, by applying the LY6H receptor or a fragment thereof to a screening for various drugs, the invention enables selecting out various compounds (which react with the LY6H receptor, inclusive of low molecular compounds, high molecular compounds, proteins, protein fragments, antigens, antibodies, etc.). Preferably, the LY6H receptor as a whole is used. The LY6H receptor polypeptide or fragment thereof for use in such screening may have been immobilized on a solid matrix or be a free substance in a solution to be transported to the cell surface.

An example of the above pharmacoscreening is a screening system in which prokaryotic or eukaryotic host cells transformed stably with a recombinant DNA coding for an LY6H polypeptide, or a fragment thereof, are used in, preferably, a competitive binding assay. As an alternative, said host cells, whether in the free form or as immobilized, are used in the standard binding assay. More particularly, the above pharmacoscreening may comprise reacting the LY6H receptor polypeptide, or a fragment thereof, with the LY6H polypeptide, or a fragment thereof, in the presence of a candidate drug, to cause formation of a complex and detecting the degree of inhibition of the complex formation by the above candidate drug.

Thus, in accordance with the invention, there can be provided a method for pharmacoscreening which comprises contacting a candidate drug with the LY6H receptor polypeptide, or a fragment thereof and, then, detecting the presence of the resulting complex or the presence of a complex of the LY6H receptor polypeptide, or a fragment thereof, with a ligand by a per se known technique. Furthermore, by assaying LY6H receptor activity, it is possible to evaluate whether a candidate drug is capable of antagonizing the LY6H receptor and accordingly may modify the above-defined LY6H activity, i.e. may be able to modulate growth of neurons, or modulate protein-protein conjugation or complex-forming activity. In such a competitive binding assay, the LY6H receptor polypeptide, or a fragment thereof, is labeled. When the free LY6H receptor polypeptide or fragment thereof is separated from the protein-protein complex and the labeling amount of the free (non-complex-forming) substance is measured, the measured value serves as a yardstick of the binding of the test factor to the LY6H receptor. The measured value serves also as a measure of inhibition of the binding of the LY6H receptor to the LY6H polypeptide. By analyzing a small peptide (pseudopeptide) of the LY6H polypeptide in this manner, the candidate drug can be assayed as a substance having LY6H receptor antagonizing activity.

Another protocol for pharmacoscreening in accordance with the invention is that of screening for a compound having an adequate binding affinity for the LY6H receptor polypeptide. Briefly, this procedure comprises synthesizing a large number of different test peptide compounds on a solid support such as the surface of a plastic pin or other material, reacting the test peptide compounds with the LY6H receptor polypeptide and, after washing, detecting the binding reaction products of LY6H receptor polypeptide by a known method [e.g. PCT patent publication No. WO 84-03564]. The purified LY6H receptor can be directly coated on the plate to be used in said pharmacoscreening procedure. The antibody may be captured with a non-neutralizing antibody against the polypeptide and the LY6H receptor polypeptide be immobilized on a solid phase.

The invention is further directed to the use of a competitive pharmacoscreening assay. For the binding to the LY6H receptor polypeptide, or a fragment thereof, a neutralizing antibody capable of specific binding to the LY6H receptor polypeptide is caused to compete with the candidate compound. By such a competitive reaction with the neutralizing antibody, the presence of any peptide having one or more antigenic determinants of the LY6H receptor polypeptide can be detected.

As a further method for drug screening, the LY6H polypeptide of the invention or the LY6H gene product of the invention can be used in the screening for compounds which activate (agonists) or inhibit (antagonists or inhibitors) the activity of the LY6H polypeptide or LY6H gene product.

By using the LY6H polypeptide or LY6H gene product of the invention, agonists or antagonists can be identified from cells, cell-free preparations, chemical libraries and naturally-occurring compositions. These agonists or antagonists may be natural or modified substrates, ligands, enzymes or receptors of the LY6H polypeptide of the invention or structural or functional copies of the polypeptide of the invention [Coligan et al., Current Protocols in Immunology, 1(2), Chapter 5 (1991)].

In situ hybridization studies revealed the expression of LY6H gene of the invention in various tissues of the human normal brain, at particularly high levels in the hippocampus and entorhinal cortex which are usually severely impaired in Alzheimer patients, and its expression level has been found to be considerably depressed in the temporal lobe inclusive of the hippocampus and entorhinal cortex of patients with Alzheimer's disease. It is, therefore, very likely that this gene is associated with the onset and progression of said disease.

Therefore, an agonist or antagonist of this LY6H protein or an LY6H gene product is expected to find application as a therapeutic or prophylactic drug for neurodegenerative diseases such as Alzheimer's disease, Alzheimer type dementia, brain ischemia and Parkinson's disease.

Compounds obtainable by the screening for candidate drugs for said LY6H gene-related diseases have the functions of the protein of the invention (the expression product of the gene of the invention), such as neuronal survival-supporting action, nerve elongating action, nerve regenerating action, neuroglia-activating action, etc. in the central and other nerve systems and brain mnemonic (memory-forming) action, among other physiological actions, and, therefore, can be used as a therapeutic or prophylactic drug for various neurodegenerative diseases such as Alzheimer's disease, Alzheimer type dementia, brain ischemia and Parkinson's disease. Thus, the proteins of the invention (inclusive of the gene expression products, partial peptides thereof, and salts thereof) are of use as reagents for the screening for compounds which promote the functions of the protein of the invention.

The invention provides a method of screening for compounds which promote the functions of the protein of the invention (hereinafter each referred to sometimes as a functional enhancer of the protein of the invention). More particularly, the invention provides (a) a method of screening for a functional enhancer of the protein of the invention which comprises contacting (1) the protein of the invention with nerve cells or a nerve tissue on one hand and (2) the protein and a test compound with said nerve cells or tissue on the other hand and comparing the results and (b) a method of screening for a functional enhancer of the protein of the invention which comprises administering (1) the protein of the invention to a vertebrate on one hand and (2) the protein of the invention and a test compound to the vertebrate on the other hand and comparing the results.

More particularly, in the above screening method (a), a physiological activity in the central or other nervous systems, such as neuronal survival-supporting activity, nerve elongating activity, nerve regenerating activity or neuroglia-activating activity, is measured under the above conditions (1) and (2) and the results are compared. In the screening method (b), the mnemonic (memory-forming) activity in the brain, for instance, is measured under said two conditions (1) and (2) and the results are compared.

The nerve cells (neurous and neuroglia) for use in the above screening include neuroblastoma cells, glioma cells, and their hybridoma cells (e.g. N18TG-2, IMR-32, GOTO (e.g. GOTO-P3), NB1, C6BU-1, U251, KNS42, KNS81 and NG108-15 cells, and PC12 cells having a potency of differentiation to nerve cells). The nerve tissue which can be used includes the mouse neuroepithelial cell, rat hippocampus primary culture cell, fetal mouse culture Prukinje cell, and mouse dorsal root ganglia. The test compound includes peptides, proteins, nonpeptide compounds, synthetic compounds, fermentation products, cell extracts, plant extracts, animal tissue extracts, and plasma. These compounds may be novel compounds or known compounds.

In carrying out said screening method (a), the protein of the invention (inclusive of a partial peptide thereof or a salt thereof) is dissolved or suspended in a screening buffer to prepare a sample of the protein of the invention. The buffer may be any buffer solution that does not interfere with the contact between the protein of the invention and the nerve cell or tissue (e.g. phosphate buffer, Tris-HCl buffer, etc. at pH about 4-10, preferably pH about 6-8). The duration of contact is usually about 1-10 days, preferably about 7-10 days. The contact temperature is usually about 37° C. The activities of the protein of the invention in the central or other nervous systems, such as neuronal survival-supporting activity, nerve elongating activity, nerve regenerating activity, and neuroglia-activating activity, can be determined by the routine methods such as visual assessment of axonal elongation, measurement of intracellular $Ca^{2+}$ concentration, and the like.

Any test compound promoting any of said physiological activities, such as neuronal survival-supporting activity, nerve elongating activity, nerve regenerating activity, neuroglia-activating activity, by at least about 20%, preferably not less than about 30%, more preferably not less than about 50%, still more preferably not less than about 70%, under the above-mentioned condition (2) as compared with the condition (1) can be selected as a functional enhancer of the protein of the invention.

In carrying out the above screening method (b), the protein of the invention, alone or in combination with the test compound, is administered to test animals by intravenous, subcutaneous or intramuscular injection or orally. The dosage of the protein of the invention for oral administration is generally about 0.1-100 mg/day, preferably about 1.0-50 mg/day, more preferably about 1.0-20 mg/day, per mammal (based on 50 kg body weight). The parenteral dose should be selected according to the recipient and the method of administration but it is preferable to administer about 0.01-30 mg/day, preferably about 0.1-20 mg/day, more preferably about 0.1-10 mg/day, per mammal (50 kg body weight) by the intravenous route.

Test animals include such mammals as man, monkey, chimpanzee, mouse, rat, rabbit, sheep, swine, bovine, horse, cat and dog and fish (e.g. carp, salmon, herring, rainbow trout, goldfish, etc.).

The memonic (memory-forming) activity of the protein of the invention in the brain can be assayed in accordance with, for example, a water maze test protocol [Morris, R. G. M., J. Neurosci. Meth., 11, 47-60 (1984)]. Any test compound promoting the above mnemonic effect by not less than about 20%, preferably not less than 50%, more preferably not less than 70%, under said condition (2) as compared with said condition (1) is of use as a functional enhancer of the protein of the invention.

The screening kit as a further embodiment of the invention contains the protein of the invention (inclusive of the expression product of the gene, a partial peptide thereof, and any salt of either of them) as an essential component. A kit consists of the following components 1-4 is an example of the screening kit of the invention.

Component 1: Hanks solution as assay buffer

Component 2: Protein standard (protein of the invention or a salt thereof)

Component 3: Nerve cells or a nerve tissue (a culture of said nerve cells or nerve tissue in a 24-well plate, $10^4$ cell/well, as grown using Eagle's MEM, Hanks solution under 5% $CO_2$ at 37° C.)

Component 4: An inverted microscope for observation The screening with the above screening kit can be carried out as follows.

[Method]

The number per field of vision of axonal elongation-positive cells in the well containing the test compound is counted and compared with the number of axonal elongation-positive cells in the control (test compound-free) well and the difference is statistically tested.

The compound or salt obtained by the screening method or with the screening kit in accordance with the invention is a member selected from the above-mentioned class consisting of peptides, proteins, nonpeptide compounds, synthetic compounds, fermentation products, cell extracts, plant extracts, animal tissue extracts, etc. and is a compound capable of promoting the function of the protein of the invention. The compound that promotes the functions of the protein of the invention as such may show physiological activities such as neuronal survival-supporting activity, nerve elongating activity, nerve regenerating activity, neuroglia-activating activity, etc. and thereby promote the function of the protein of the invention or the like additively or synergistically or, although not showing such physiological activities by itself, may promote the function of the protein of the invention. Examples of the salts of the compound include salts with physiologically acceptable bases (e.g. alkali metals) or acids (e.g. organic acids, inorganic acids). Particularly preferred are physiologically acceptable acid addition salts, such as salts with inorganic acids (e.g. hydrochloric acid, phosphoric acid, hydrobromic acid, sulfuric acid) or organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The compound or salt which promotes the function of the protein of the invention is of value as a safe, low-toxicity therapeutic-prophylactic drug for various neurodegenerative diseases such as Alzheimer's disease, Alzheimer type dementia, brain ischemia and Parkinson's disease.

The above screening procedure involves the use of cells which express the LY6H polypeptide on the cell surface or respond to the protein of the invention. Among such cells are cells derived from mammalian animals, yeasts, *Drosophilia* and *E. coli*. The cells which express the LY6H polypeptide (or the cell membrane having the expressed polypeptide) or respond to the LY6H polypeptide is contacted with the test compound to observe the stimulation or inhibition of binding or functional response. Then, LY6H activity of cells contacted with the candidate compound is compared with that of similar cells not contacted.

The above assay can be carried out by detecting adhesion to cells harboring the LY6H polypeptide using a label directly or indirectly coupled to a candidate compound or in an assay system utilizing a competition with a label-competitive substance. In this manner, the binding of the candidate compound can be easily tested. Furthermore, using a detection system suited to cells bearing the LY6H polypeptide in such assays, it may be tested whether the candidate compound will produce a signal ascribable to activation of the LY6H polypeptide. The activation inhibitor is generally assayed in the presence of a known agonist and the effect of the candidate compound on the activation due to the agonist is observed. The assay may comprise a simple procedure comprising mixing the candidate compound with a solution containing the LY6H polypeptide to form a mixture, determining the LY6H activity in the mixture, and comparing the LY6H activity of the mixture with a standard.

The low molecular compound (agonist or antagonist) which binds to the LY6H protein can be obtained by a screening with BIACORE 2000, for instance [Markgren, P. O., et al., Analytical Biochemistry, 265, 340-350 (1998)].

In accordance with the invention, for the purpose of developing a more active or stabilized LY6H polypeptide derivative or a drug which enhances or blocks the function of the LY6H polypeptide in vivo, it is possible to construct a biologically active polypeptide or a structural analog thereof for interaction, such as an LY6H agonist, LY6H antagonist, LY6H inhibitor or the like. The structural analog mentioned above can be obtained, for example, by determining the three-dimensional structure of a complex of LY6H polypeptide with another protein by X-ray crystallography, computer modeling or a combination of such techniques. Information on the structure of a structural analog can also be acquired by polypeptide modeling based on the structures of homologous proteins.

To obtain said more active or stabilized LY6H polypeptide derivative, analysis by alanine scan can be employed. This method comprises substituting Ala for each amino acid residue to assess the influence of substitution on peptide activity. Thus, as each amino acid residue of a peptide is thus analyzed, the region of importance to the activity or stability of the peptide is determined. By this method, it is possible to design a more active or stable LY6H polypeptide derivative.

It is also possible to isolate the target-specific antibody selected by the functional assay and analyze its crystal structure. As a rule, by this approach, the pharmacore providing a basis for subsequent drug design is obtained. By producing an anti-ideotypic antibody to the functional pharmacologically active antibody, it is possible to identify and isolate a peptide from a chemically or biologically generated peptide bank. Therefore, it is predictable that the selected peptide may also serve as a pharmacore.

In this manner, it is possible to design and develop drugs having improved or stabilized LY6H activity or acting as inhibitors, agonists or antagonists of LY6H activity.

Evaluation of such a drug can be made by titrating its effect on neuronal survival using primary culture hippocampal neurons [Japan. J. Pharmacol, 53, 221-227 (1990)] or investigating its effect on neurodegenerative lesions in Alzheimer model animals such as mutant β-amyloid precursor protein gene or mutant presenilin 1 gene transgenic mice [Nature, 373, 523-527 (1995): Nature Med., 5, 560-564 (1999)].

The compound thus obtained can be used not only as a drug for Alzheimer's disease but also as a therapeutic drug for cerebral infarction and other neurodegenerative diseases.

Furthermore, in accordance with the invention, by constructing LY6H gene-bearing knockout mice (transgenic mice with LY6H knockout backgrounds), it is possible to ascertain which site or sites of the nucleotide sequence of the LY6H gene have influences on said multiple LY6H activities in vivo, that is to say what functions the expression products of LY6H gene and of a modified LY6H gene have in vivo.

This method is a technique to intentionally modify the genetic information of a living thing by utilizing homologous recombinant genes, and includes a method using mouse embryonic stem cells (ES cells) as an example [Capeccchi, M. R., Science, 244, 1288-1292 (1989)].

The method of constructing said mutant mice is by now a routine technology for those skilled in the art, and mutant mice can be easily constructed by applying a human wild-type Ly6H gene or a mutant LY6H gene to a modified version of the above technology [Noda, Testuo (ed.): Jikken Igaku (Experimental Medicine), Supplement, 14(20) (1996), Y ōdosha). Therefore, by utilizing this technique, it is possible to design and develop drugs having improved or stabilized LY6H activity or inhibitors, agonists, and antagonists of LY6H activity.

BEST MODE FOR CARRYING OUT THE INVENTION

Figure 1:
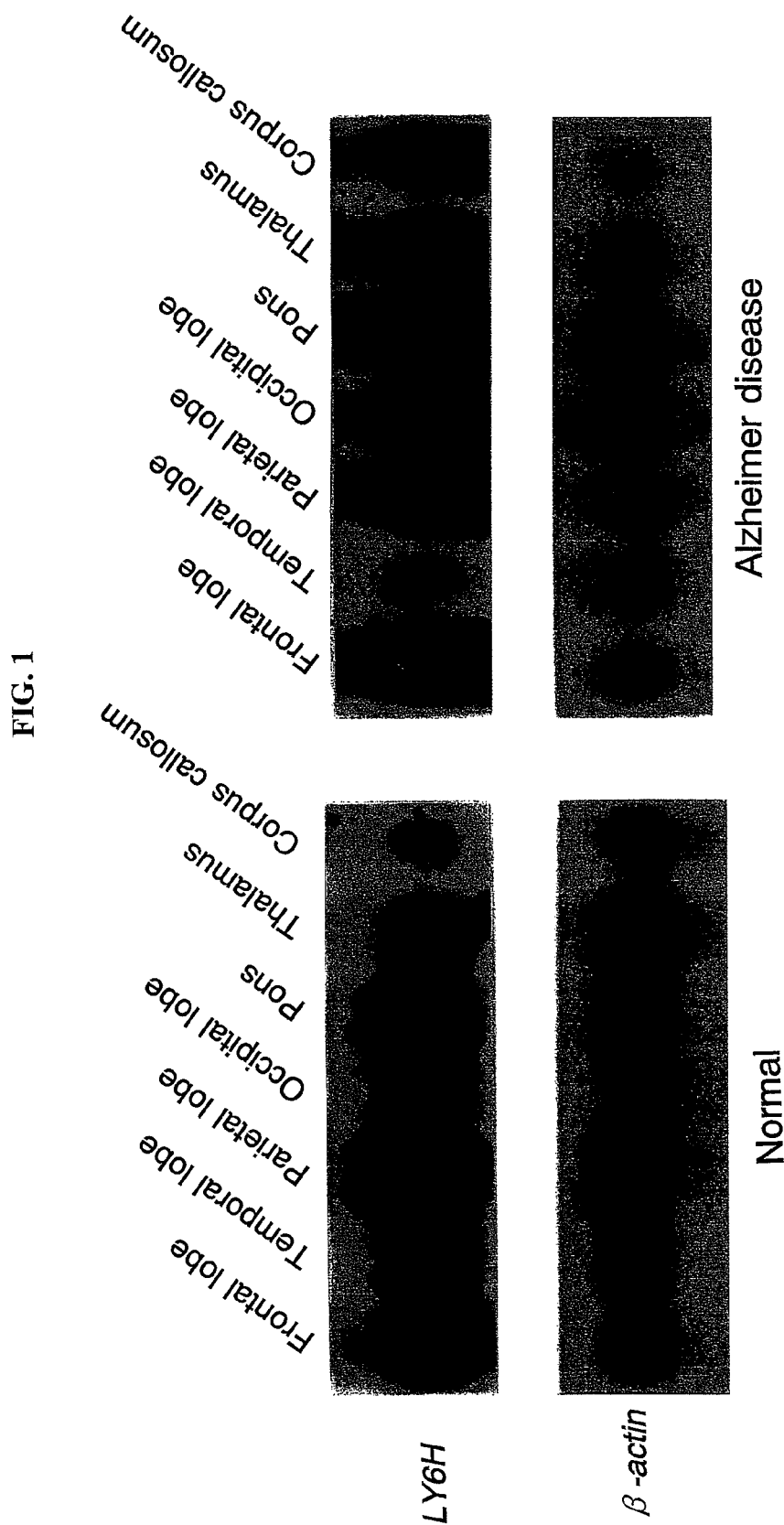
FIG. 1 is a diagrammatic representation of Northern blots showing the pattern of expression of LY6H gene in various sites of the brain of a patient with Alzheimer's disease.

The following examples are intended to illustrate the invention in further detail.

EXAMPLE 1

(1) Cloning and DNA Sequencing of Human LY6H Gene

The mRNA extracted from the human fetal brain was purchased from CLONTECH Laboratories and used as the starting material. From this mRNA, a cDNA was synthesized and ligated into the vector XZAPII (Stratagene) to construct a cDNA library (Otsuka GEN Research Institute, Otsuka Pharmaceutical Co.). Using the in vivo excision method [in vivo excision: Short, J. M., et al., Nucleic Acids Res., 16, 7583-7600 (1988)], colonies of *Escherichia coli* bearing the human gene were formed on agar medium and randomly picked up to register the human gene-bearing *E. coli* clones in a 96-well microplate. These clones were stored at −80° C.

Then, each registered clone was cultured in 1.5 ml of LB medium overnight and the DNA was extracted and purified using an automatic plasmid extractor PI-100 (Kurabo). The contaminated *E. coli* RNA was decomposed with RNase and removed. Finally, 30 μl of a DNA solution was prepared and using a 2 μl portion, the approximate DNA size and amount were checked by the minigel method. A 7 μl portion was used for a sequencing reaction and the remaining 21 μl was stored as plasmid DNA at 4° C. By this method, a cosmid which can also be used as a probe for FISH (fluorescence in situ hybridization) described below can be extracted by a minor modification of the program.

Then, a dideoxy terminator reaction of Sanger et al. using T3, T7 or a synthetic oligonucleotide primer [Sanger, F., et al., Proc. Natl. Acad. Sci., USA., 74, 5463-5467 (1977)] or a cycle sequencing reaction [Carothers, A. M., et al., Bio. Techniques, 7, 494-499 (1989)] which is the dideoxy terminator reaction plus PCR was carried out. These are techniques for chain extension with termination specific to 4 kinds of bases using a small amount (about 0.1-0.5 μg) of plasmid DNA as the template.

Using an FITC (fluorescein isothiocyanate)-labeled primer as the sequence primer, about 25 cycles of reaction using Taq polymerase were carried out. Of the fluorescence-labeled DNA fragment, the sequence of about 400 nucleotides from the 5'-end of the cDNA was determined with the automatic DNA sequencer ALF™ DNA Sequencer (Pharmacia).

The 3'-nontranslated region is high in heterogeneity among genes and suited for differentiation of individual genes. Therefore, sequencing of the 3'-end region was also performed in some cases.

The huge nucleotide sequence information generated with the DNA sequencer was transmitted to the 64-bit computer DEC3400 for computerized homology analysis. This homology analysis was carried out by a database (GenBank, EMBL) search according to UWGCG's FASTA Program [Pearson, W. R. and Lipman, D. J., Proc. Natl. Acad. Sci., USA., 85, 2444-2448 (1988)].

Fujiwara et al. describe in detail about the above method of analysis for a human fetal brain cDNA library [Fujiwara, T., et al., DNA Res., 2, 107-111 (1991)].

The ESTs (expressed sequence tags: partial DNA sequences of the expressed gene fragment) randomly selected from the human fetal brain cDNA library constructed as above were then sequenced.

The clone designated GEN-425D01 in the GenBank/EMBL sequence search according to the FASTA Program was found to be highly homologous to the gene coding for the mouse Ly6 family protein.

Using a double-stranded DNA inserted into a vector (pBluescript vector; Stratagene) as a template and a synthetic oligonucleotide as a primer, the nucleotide sequence of the cDNA inclusive of the whole coding region of the above clone was determined by Sanger's dideoxy chain termination method.

Sequencing with ABIPRISM™377 automatic DNA sequencer revealed that the cDNA sequence of the clone obtained above contained a deduced amino acid coding region of 420 bases and the amino acid sequence encoded thereby had 140 amino acid residues. The nucleic acid sequence of the full-length cDNA clone was composed of 854 nucleotides. The full sequence is shown in SEQ ID NO:3; the nucleotide sequence of the open reading frame is shown in SEQ ID NO:2; and the deduced amino acid sequence encoded by said nucleotide sequence is shown in SEQ ID NO:1.

The amino acid sequence of the human LY6H protein was compared with the sequences of other Ly6 family proteins, and the nucleotide sequence conserved in the amino acid translation initiation region [Kozak, M., J. Biol. Chem., 266, 19867-19870 (1991)] was compared with the 5'-region of the human LY6H gene. The initiation codon thus determined was located in the position 99-101, which is the second ATG triplet, of the nucleotide sequence shown in SEQ ID NO:3. Moreover, the polyadenylation signal (AATAAA) was located in the position 832-837 of the same nucleotide sequence.

(2) Northern Blot Analysis

To define the expression profile of LY6H in tissues, a Northern blot analysis was performed using various human tissues.

In the Northern blot analysis, Human MTN (Multiple-Tissue Northern) Blot I and II (CLONTECH) were used.

The cDNA fragment was amplified by PCR using a primer set of T3 and T7 promoter sequences.

The PCR amplification product of said GEN-425D01cDNA clone was labeled with [$^{32}$P]-dCTP (Random Primed DNA Labeling Kit, Boehringer Mannheim GmbH) for use as a probe.

The blot containing the amplification product was prehybridized (under conditions according to the product protocol) and, then, subjected to hybridization according to the product protocol.

The hybridization was performed at 65° C. overnight in a solution composed of 1 M NaCl/50 mM Tris-HCl (pH 7.5)/2×Denhardt's solution/10% dextran sulfate/1% SDS solution (containing 100 μg/ml denatured salmon sperm DNA). After wash twice with 2×SSC/0.1% SDS at room temperature, the product was washed once with 0.1×SSC/0.1% SDS at 65° C. for 40 minutes. The filter was exposed against X-ray film (Kodak) at −70° C. for 18 hours.

The above test was performed using the following adult human tissues: brain, pancreas, testis, small intestine, colon, thymus, prostate, ovary, heart, placenta, lung, liver, skeletal muscle, kidney, spleen, testis and peripheral blood leukocyte. As a result, transcripts of about 1 kb showing homology to LY6H were observed in the brain, pancreas, testis, small intestine, colon, thymus, prostate and ovary, particularly high in the brain.

(3) Localization of the Gene on Chromosome by FISH Using Cosmid Clones

FISH for chromosomal localization was carried out using 0.5 μg of each cosmid DNA as a probe in accordance with the known method [Takahashi, E. et al., Hum. Genet., 86, 14-16 (1990)]. It was caught FISH signals by Provia 100 film (Fuji, ISO 100) or CCD Camera System (Applied Imaging Cyto Vision).

As a result, the human LY6H gene was found to be located on q24.3 of chromosome 8. Thus, GEN-425D01 was mapped on the chromosome band 8q24.3.

The antibodies against proteins belonging to the Ly6 family have been utilized in the purification of blood stem cells as a target of gene therapy [van de Rijn, M., et al., Proc. Natl. Acad. Sci., USA., 86, 4634-4638 (1989)], studies on the differentiation of blood cells [van de Rijn, M., et al., Proc. Natl, Acad. Sci., USA., 86, 4634-4638 (1989); Classon, B. J. and Coverdale, L., Proc. Natl. Acad. Sci., USA., 91, 5296-5300 (1994)], activation of immune cells [Malek, T. R., et al., J. Exp. Med., 164, 709-722 (1986)], inhibition of production of active immune cells [Haque, A., et al., Immunology, 69, 558-563 (1990)], and the like, and have also been found to have antitumor effects [Lu, L., et al., J. Immunol., 142, 719-725 (1989)]. The human LY6H gene provided in the present example enables detection of the expression of the gene in various tissues, production of the human LY6H protein by genetic engineering techniques, and construction of an antibody by utilizing the gene, hence enabling said purification of blood stem cells, research into the differentiation of blood cells, activation of immune cells, inhibition of activation of immune cells, and therapy of tumors.

Furthermore, the LY6H expressed at a high level in the brain enables a research into the differentiation of nerve cells, activation of neurons, and therapy of neural and mental diseases.

Screening for compounds with the human LY6H protein as the target is also made possible and the compounds thus obtained are as useful as the anti-human LY6H protein antibody.

EXAMPLE 2

(1) Northern Blot Analysis in the Brain Tissues of a Patient with Alzheimer's Disease Northern Blot Analysis was Performed in Accordance with Example 1 (2)

To investigate the expression of the LY6H gene in the brain tissues of patients with Alzheimer's disease, Northern blot analysis was made using the brain tissues of an Alzheimer patient and normal human brain tissues.

Northern blotting was performed using the human normal brain blot II and human Alzheimer blot II (both Invitrogen) and the LY6H gene expression in the various brain tissues, namely the frontal lobe, temporal lobe, parietal lobe, occipital lobe, pons, thalamus and corpus callosum, was compared between normal and Alzheimer brains.

The results are shown in FIG. 1.

As was pointed out in Example 1, the LY6H gene is expressed at a high level in the brain. The above analysis revealed that, while the expression of the gene was confirmed in various tissues of the human normal brain, the gene was expressed at particularly high levels in the temporal lobe inclusive of the hippocampus and entorhinal cortex which are known to be impaired severely in patients with Alzheimer's disease while marked decreases were found in the temporal lobe inclusive of the hippocampus and entorhinal cortex in the patient with Alzheimer's disease, indicating that it is very likely that the gene is involved in the onset and progression of this disease.

Therefore, the LY6H gene sense strand, LY6H expression product, and LY6H protein are expected to find application as therapeutic drugs for Alzheimer's disease, Alzheimer type dementia, brain ischemia and Parkinson's disease.

Furthermore, agonists and antagonists of LY6H protein are also expected to be of use as therapeutic drugs for Alzheimer's disease and other diseases.

EXAMPLE 3

(1) Construction of an LY6H Expression Vector

The LY6H cDNA obtained by in vivo excision method is cleaved with MvII and XhoI to give an about 800-base fragment. This fragment, containing the entire coding region of the LY6H gene shown in SEQ ID NO:1, is ligated to the EcoRV/XhoI-cleaved pAc5.1/V5-HisA (Invitrogen) to construct an expression vector (pAC/LY6H expression vector).

(2) Expression and Purification of the Active Ingredient Protein of the Invention The pAC/LY6H expression vector DNA and pCoHYGRO vector (Invitrogen) DNA are admixed in a ratio of 19:1 and introduced into fruit fly (Schneider 2) cells by calcium phosphate transfection. After the cells are cultured in 10% fetal calf serum-DES expression medium (Invitrogen) at 23° C. for 48 hours, 300 µg/ml of hygromycin (Hygromycini B, Boehringer Mannheim) is added to the culture and the selection of drug-resistant cell clones is performed for 2 weeks. A stable transformant is subjected to stationary culture at a concentration of $5\times10^6$ cells/ml using 20 Falcon 5000 culture flasks (Becton Dickinson) containing 20 ml of 10% fetal calf serum-DES expression medium (Invitrogen) and the cultured cells are harvested. After washing twice with phosphate-buffered saline (PBS), the cells are suspended in PBS containing 2% bovine serum albumin and 0.5 U/ml of phosphatidyl-inositol-specific phospholipase C (PIPLC) and cultured at 37° C. for 1 hour. From the supernatant of the culture, the objective protein can be purified by ion exchange column chromatography or the like.

(3) Isolation and Culture of Hippocampal Neurons

The whole brain is aseptically isolated from fetal SD rats on embryonic day 18 and the hippocampus is excised. The excised tissue is cut to thin slices with a surgical knife and incubated for enzymatic treatment in PBS containing 0.25% trypsin and 0.002% DNase I at 37° C. for 20 minutes. After the enzymatic reaction is stopped by adding fetal calf serum, the aspiration-ejection of the cell digest with a pipette having a plastic tip is repeated 3 times to disperse the cells. The cell dispersion is passed through a filter consisting of 2 stacked sheets of lens paper to remove the undigested tissue and centrifuged at 1000 rpm for 5 minutes. The cells are washed with DMEM (Gibco) and seeded on a poly-L-lysine (Sigma)-coated 96-well plate containing 10% FCS-DMEM at a final concentration of $2\times10^5$ cells/cm$^2$.

(4) Treatment with the Active Ingredient Protein of the Invention

The above cells are cultured for 24 hours and after the culture medium is changed to 1% N$_2$ Supplement (Gibco)-DMEM, the active ingredient protein of the invention as prepared under (2) is added (the invention group).

For comparison, the active ingredient protein of the invention is heat-treated in a boiling water bath for 5 minutes and added (the boiled protein group).

(5) Evaluation of Hippocampal Neuronal Survival

The cells (culture) in each group as prepared under (4) are cultured for 72 hours. Then, the hippocampal neuronal survival-supporting effect of the active ingredient protein of the invention can be evaluated by the MTT [3-(4,5-dimethylthiazol-2-yl)-2,5-diphenyltetrazolium bromide] assay. This MTT assay may be performed using Promega's "CellTiter 96" Assay System, for instance.

(6) Isolation and Culture of Midbrain Neurons

The whole brain is aseptically isolated from fetal SD rats on embryonic day 14 and the ventral midbrain is excised. The tissue is cut to thin slices with a surgical knife and incubated for enzymatic treatment in phosphate-buffered saline (PBS) containing 0.25% trypsin and 0.002% DNase I at 37° C. for 20 minutes. After the enzymatic reaction is stopped by adding fetal calf serum, the aspiration-ejection of the cell digest with a pipette having a plastic tip is repeated 3 times to disperse the cells. The cell dispersion is passed through a filter consisting of 2 stacked sheets of lens paper to remove the undigested tissue and centrifuged at 1000 rpm for 5 minutes. The cells are washed with DMEM/F12 (Gibco) and seeded on a poly-L-lysine-coated 96-well plate containing 10% FCS-DMEM/F12 at a final concentration of $3\times10^5$ cells/cm$^2$.

(7) Treatment with the Active Ingredient Protein of the Invention

The cells prepared under (6) are cultured for 24 hours and after the culture medium is changed to 1% N$_2$ Supplement (Gibco)-DMEM/F12, the active ingredient protein of the invention as prepared under (2) is added (the invention group).

For comparison, the active ingredient protein of the invention is heat-treated in a boiling water bath for 5 minutes and added (the boiled protein group).

(8) Evaluation of Midbrain Neuronal Survival Supporting Effect

The cells (culture) in each group as prepared under (7) are cultured for 72 hours. Then, the midbrain neuronal survival-supporting effect of the active ingredient protein of the invention can be evaluated by the MTT [3-(4,5-dimethylthiazol-2-yl)-2,5-diphenyltetrazolium bromide] assay. This MTT assay may be performed using Promega's "CellTiter 96" Assay System, for instance.

(9) Evaluation of Dopaminergic Neuronal Survival-supporting Effect

The cells (culture) in each group as prepared under (7) are cultured for 72 hours and, then, fixed by allowing them to stand in 4% paraformaldehyde-PBS at room temperature for 15 minutes. Thereafter, using 1% Triton X100/PBS, it is passed through a membrane.

To prevent nonspecific binding of the antibody, the cells are incubated in 10% goat serum-PBS for 1 hour and, then, using an anti-tyrosine hydroxylase polyclonal antibody (Chemicon; diluted 1000-fold with PBS), the cells are incubated at 4° C. for 16 hours. After the antibody solution is removed, the cells are washed with PBS and, with peroxidase-labeled dextran polymer-conjugated goat anti-rabbit immunoglobulin (Dako) added, the cells are incubated at room temperature for 1 hour.

The tyrosine hydroxylase-positive cells can be detected by the color reaction using diaminobenzidine as the substrate. Using the number of tyrosine hydroxylase-positive cells as a marker, the dopaminergic neuronal survival-supporting effect can be evaluated.

INDUSTRIAL APPLICABILITY

The present invention provides a novel brain-specific gene and a protein encoded thereby and, by utilizing them, technologies of value to the purification of blood stem cells, research into the differentiation of blood cells, activation of immune cells, inhibition of production of active immune cells, and therapy of tumors can be provided. Also, the present invention provides novel genes having physiologic activities such as brain neuronal survival-supporting activity, nerve elongating activity, nerve regenerating activity, neuroglia-activating activity and brain memory-forming activity.

In view of the marked depression of its expression level in the temporal lobe of the brain of patients with Alzheimer's disease, the gene of the invention is considered to inhibit neurodegenerative changes of the tissue, thus being of use as a gene therapy drug. Moreover, the expression product of the gene of the invention finds application as a prophylactic and therapeutic drug for such neurodegenerative diseases.

The invention claimed is:

1. An isolated polypeptide consisting of the amino acid sequence of SEQ ID NO: 1.

2. A recombinant protein consisting of an amino acid sequence encoded by the nucleotide sequence of SEQ ID NO:2 or the nucleotide sequence of SEQ ID NO:3.

* * * * *